United States Patent
Simon et al.

(10) Patent No.: US 10,743,822 B2
(45) Date of Patent: Aug. 18, 2020

(54) FIDUCIAL MARKER FOR GEOMETRIC CALIBRATION OF BED-SIDE MOBILE TOMOSYNTHESIS SYSTEM

(71) Applicant: CARESTREAM HEALTH, INC., Rochester, NY (US)

(72) Inventors: Richard A. Simon, Rochester, NY (US); Levon O. Vogelsang, Webster, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 116 days.

(21) Appl. No.: 16/022,864

(22) Filed: Jun. 29, 2018

(65) Prior Publication Data
US 2020/0000426 A1   Jan. 2, 2020

(51) Int. Cl.
*A61B 6/00* (2006.01)
*A61B 6/02* (2006.01)
*A61B 6/03* (2006.01)

(52) U.S. Cl.
CPC .............. *A61B 6/025* (2013.01); *A61B 6/032* (2013.01); *A61B 6/40* (2013.01); *A61B 6/42* (2013.01); *A61B 6/4208* (2013.01); *A61B 6/4283* (2013.01); *A61B 6/44* (2013.01); *A61B 6/4405* (2013.01); *A61B 6/4411* (2013.01); *A61B 6/4429* (2013.01); *A61B 6/4452* (2013.01); *A61B 6/465* (2013.01); *A61B 6/54* (2013.01); *A61B 6/547* (2013.01); *A61B 6/58* (2013.01); *A61B 6/582* (2013.01); *A61B 6/584* (2013.01); *A61B 6/587* (2013.01); *A61B 6/588* (2013.01); *A61B 6/589* (2013.01)

(58) Field of Classification Search
CPC ......... A61B 6/025; A61B 6/40; A61B 6/4007; A61B 6/42; A61B 6/4208; A61B 6/4283; A61B 6/44; A61B 6/4405; A61B 6/4411; A61B 6/4429; A61B 6/4452; A61B 6/54; A61B 6/547; A61B 6/58; A61B 6/582; A61B 6/583; A61B 6/584; A61B 6/587; A61B 6/588; A61B 6/589
USPC ....................... 378/21–26, 62, 196–198, 207
See application file for complete search history.

(56) References Cited

U.S. PATENT DOCUMENTS

| | | | | |
|---|---|---|---|---|
| 5,359,637 A * | 10/1994 | Webber | .................. | A61B 6/025 378/162 |
| 6,028,910 A * | 2/2000 | Kirchner | .............. | G01N 23/046 378/22 |
| 6,081,577 A * | 6/2000 | Webber | ................ | G01N 23/046 378/23 |
| 6,289,235 B1 * | 9/2001 | Webber | .................... | A61B 6/12 378/23 |

(Continued)

*Primary Examiner* — Allen C. Ho

(57) ABSTRACT

A method for geometric calibration of a radiography apparatus disposes at least one radio-opaque marker in the field of view of the radiography apparatus. A series of tomosynthesis projection images of patient anatomy is acquired from the detector with the x-ray source at different positions along a scan path. For at least three projection images showing the position of the radio-opaque marker, the spatial and angular geometry of the x-ray source and detector are calculated according to the positions of the marker. A tomosynthesis image is reconstructed according to the calculated geometry. A rendering of the reconstructed image is displayed.

18 Claims, 31 Drawing Sheets

(56) References Cited

U.S. PATENT DOCUMENTS

| | | | |
|---|---|---|---|
| 6,888,924 B2 * | 5/2005 | Claus | A61B 6/583 378/163 |
| 7,099,428 B2 * | 8/2006 | Clinthorne | A61B 6/14 378/17 |
| 7,147,373 B2 * | 12/2006 | Cho | A61B 6/547 378/207 |
| 7,447,295 B2 * | 11/2008 | Hoheisel | A61B 6/032 378/4 |
| 7,567,647 B1 * | 7/2009 | Maltz | A61B 6/025 378/21 |
| 7,664,222 B2 | 2/2010 | Jabri et al. | |
| 7,711,087 B2 * | 5/2010 | Mostafavi | A61B 6/025 378/22 |
| 7,831,013 B2 * | 11/2010 | Star-Lack | A61N 5/1049 378/23 |
| 7,831,296 B2 * | 11/2010 | DeFreitas | A61B 6/502 600/427 |
| 7,950,849 B2 * | 5/2011 | Claus | G06T 11/005 378/18 |
| 8,007,173 B2 * | 8/2011 | Paidi | A61B 6/584 378/207 |
| 8,396,188 B2 * | 3/2013 | Liu | A61B 6/4283 378/62 |
| 8,576,986 B2 * | 11/2013 | Liu | G01T 1/24 378/98.8 |
| 8,693,622 B2 * | 4/2014 | Graumann | A61B 6/025 378/19 |
| 8,768,026 B2 * | 7/2014 | Ren | A61B 6/0414 382/131 |
| 8,804,912 B2 * | 8/2014 | Akahori | A61B 6/025 378/163 |
| 8,903,039 B2 * | 12/2014 | Masumoto | A61B 6/5205 378/21 |
| 9,270,904 B2 * | 2/2016 | Hammond | H04N 5/32 |
| 9,380,985 B2 * | 7/2016 | Akahori | A61B 6/025 |
| 9,408,579 B2 * | 8/2016 | Yamakawa | A61B 6/14 |
| 9,526,471 B2 * | 12/2016 | Goodenough | A61B 6/025 |
| 9,532,752 B2 * | 1/2017 | Goossen | A61B 6/0414 |
| 9,541,509 B2 * | 1/2017 | Akahori | A61B 6/486 |
| 9,649,074 B2 * | 5/2017 | Simon | A61B 6/025 |
| 9,655,577 B2 * | 5/2017 | Choi | A61B 6/025 |
| 9,675,277 B2 * | 6/2017 | Arai | A61B 5/1075 |
| 9,782,136 B2 * | 10/2017 | Zhou | A61B 6/547 |
| 9,872,663 B2 * | 1/2018 | Duewer | A61B 6/027 |
| 10,016,173 B2 * | 7/2018 | Foos | A61B 6/4405 |
| 10,111,625 B2 * | 10/2018 | Toba | A61B 10/0233 |
| 10,517,561 B2 * | 12/2019 | Lin | A61B 6/582 |
| 10,631,818 B2 * | 4/2020 | Vogelsang | A61B 6/52 |
| 2016/0220212 A1 | 8/2016 | Duewer | |

* cited by examiner

| Patient Name | Location | Exam | Exam Time |
|---|---|---|---|
| James Johnson | Rm 203 | Portable Chest | 4/11/2010 11:23:51 AM |
| Fred Smith | Rm 224 | Knee | 4/11/2010 11:24:12 AM |
| Fred Jones | Rm 245 | Portable Chest | 4/11/2010 11:23:44 AM |
| Scott Smith | Rm 252 | Portable Hip | 4/11/2010 11:24:05 AM |
| John Jones | Rm 483 | Portable Hip | 4/11/2010 11:22:48 AM |
| Bill Miller | Rm 508 | Portable Hip | 4/11/2010 11:23:37 AM |
| Bill Smith | Rm 572 | Knee | 4/11/2010 11:23:30 AM |
| Bill Miller | Rm 778 | Portable Chest | 4/11/2010 11:23:16 AM |
| Mike Jones | Rm 884 | Knee | 4/11/2010 11:23:23 AM |
| Robert Jones | Rm 944 | Portable Hip | 4/11/2010 11:23:02 AM |
| Fred Johnson | Rm 993 | Knee | 4/11/2010 11:23:58 AM |

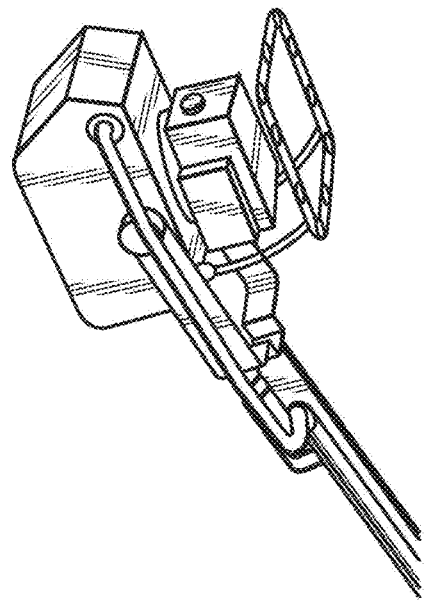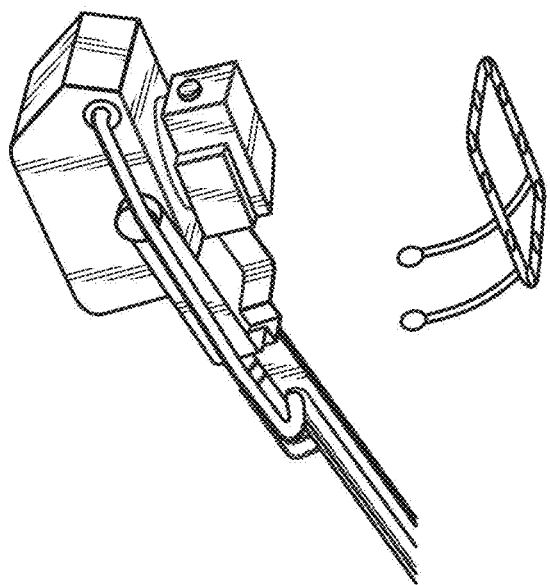
FIG. 19

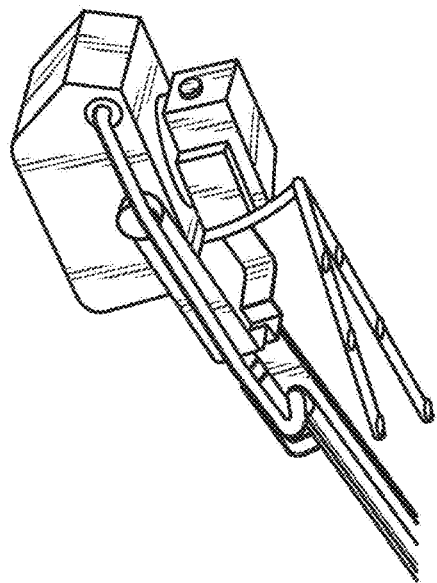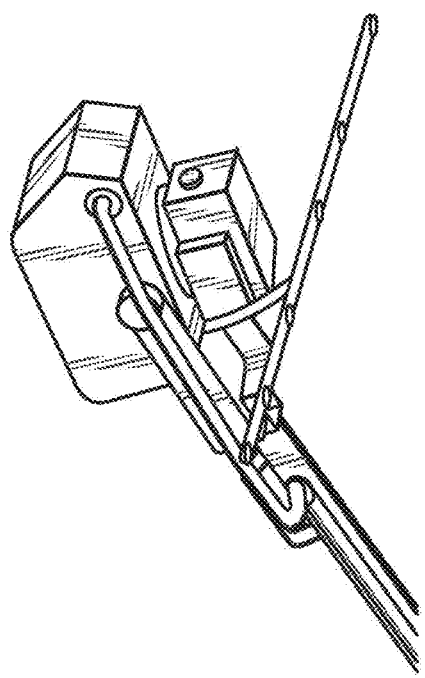
FIG. 20

FIDUCIAL MARKER FOR GEOMETRIC CALIBRATION OF BED-SIDE MOBILE TOMOSYNTHESIS SYSTEM

TECHNICAL FIELD

The disclosure relates generally to the field of medical imaging, and in particular to radiographic imaging apparatus. More specifically, the disclosure relates to geometric calibration of a mobile radiography apparatus having tomosynthesis capability.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the orientations of the x-ray tube, patient and detector. This is usually accomplished by either moving both the detector and x-ray source or by fixing the position of the detector (source) and moving the x-ray source (detector). In applications where the detector is fixed, multiple spatially distributed X-ray sources may alternately be used, or movable sources may be displaced in various patterns or trajectories. Three-dimensional data is reconstructed from the captured projections in the form of a number of slices through the patient anatomy, each parallel to the detector plane. A consequence of limited angular scanning is that the in depth resolution is much lower than the in-plane resolution of the reconstructed object.

Reconstruction of volumetric data from a tomosynthesis system requires knowledge of the underlying capture geometry, including the relative orientation and position of the detector, the movement and position of the source for each projection, and potential patient motion. In a standard tomosynthesis apparatus, many of the geometric variables are well known, as the detector position is precisely specified, and the relationship between source and detector is mechanically fixed and well established.

For a bed-side portable tomosynthesis system, however, the capture geometry can be difficult to determine with the desired accuracy. Detector positioning is done by the operator with consideration for affording the patient a reasonable degree of comfort, but without a high degree of geometric precision. The detector is placed behind a patient by an attending operator, so that often the detector is completely obscured by the patient's body. For instance, the patient may be in a propped position, with the detector placed behind the patient. The angle between the detector plane and a horizontal plane is only approximately known. Moreover, the detector might be skewed with respect to the transport path of the x-ray source, which further complicates the reconstruction process. The result is that the image quality of the resulting volumetric data can be compromised.

There is a need for a calibration utility that overcomes the limitations aforementioned and more accurately defines the geometry of the tomosynthesis system when using mobile radiography apparatus.

SUMMARY

An aspect of this application is to advance the art of radiography tomosynthesis systems.

Another aspect of this application to address in whole or in part, at least the foregoing noted problems and other deficiencies in the related art.

It is another aspect of this application to provide in whole or in part, at least the advantages described herein.

Another aspect of the application is to provide methods and/or apparatus by which mobile radiography carts can additionally include tomosynthesis capabilities.

Another aspect of the application is to provide methods and/or apparatus embodiments by which mobile radiography carts can acquire projection images and generate reconstructed three-dimensional tomosynthesis images.

Another aspect of the application is to provide methods and/or apparatus embodiments by which mobile radiography carts can acquire x-ray tomosynthesis projection images and generate the reconstruction of two-dimensional or three-dimensional tomosynthesis images where an imaging geometry of x-ray source positions relative to a radiographic detection array is not known for the plurality of x-ray tomosynthesis projection images.

These objects are given only by way of illustrative example, and such objects may be exemplary of one or more embodiments of the invention. Other desirable objectives and advantages inherently achieved may become apparent to those skilled in the art. The invention is defined by the appended claims.

According to one aspect of the disclosure, there is provided a method for geometric calibration of a radiography apparatus, the method executed at least in part by a computer and comprising: disposing at least one radio-opaque marker in the field of view of the radiography apparatus; acquiring a series of tomosynthesis projection images of patient anatomy from a detector from different x-ray source positions along a scan path; identifying at least three projection images and identifying the position of the radio-opaque marker in each of the at least three projection images; calculating the spatial and angular geometry of the x-ray source and detector according to the positions of the marker in each of the at least three projection images; reconstructing a tomosynthesis image according to the calculated geometry; and displaying a rendering of the reconstructed image.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 5-8 are diagrams that illustrate exemplary functions implemented at embodiments of a mobile x-ray imaging apparatus.

FIGS. 19-20 are diagrams that show mobile radiographic imaging systems that can include first and second (e.g., multiple) radiographic x-ray sources according to embodiments of the present disclosure.

DETAILED DESCRIPTION OF THE EMBODIMENTS

Figure 1:
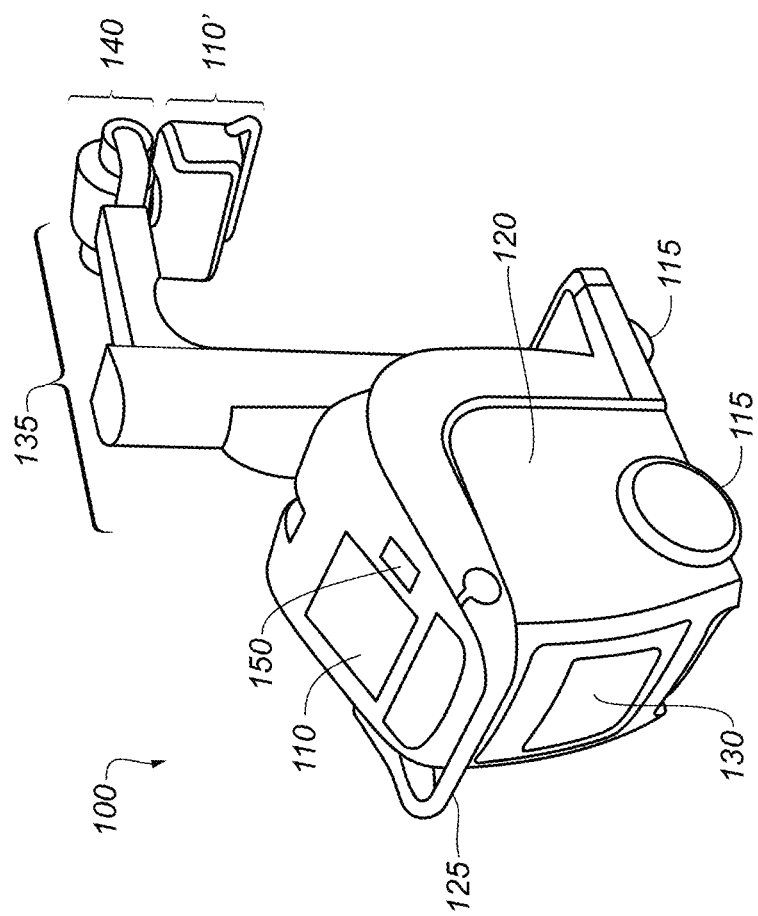
FIG. 1 is a diagram that shows a perspective view of a mobile radiography unit that can use portable radiographic detectors or flat panel detectors according to embodiments of the present disclosure.

The following is a description of exemplary embodiments of the invention, reference being made to the drawings in which the same reference numerals identify the same elements of structure in each of the several figures.

In this document, the terms "a" or "an" are used, as is common in patent documents, to include one or more than one, independent of any other instances or usages of "at least one" or "one or more". In this document, the term "or" is used to refer to a nonexclusive or, such that "A or B" includes "A but not B", "B but not A", and "A and B", unless otherwise indicated. In this document, the terms "including" and "in which" are used as the plain-English equivalents of the respective terms "comprising" and "wherein". Also, in the following claims, the terms "including" and "comprising" are open-ended, that is, a system, device, article, or process that includes elements in addition to those listed after such a term in a claim are still deemed to fall within the scope of that claim.

In the following claims, the terms "first", "second", and "third", and the like, are used merely as labels, and are not intended to impose numerical or ordinal requirements on their objects.

Portable radiographic systems are routinely used in hospitals. Compared to standard projection radiography, tomosynthesis provides improved depiction of fine details not visible in normal radiographs due to overlying structures. These benefits provide the impetus to develop portable tomosynthesis systems that can be utilized in the intensive care unit, emergency department, and operating rooms where moving the patient is either impracticable or ill-advised due to the risk of harm to the patient.

The image quality of the reconstruction depends, in part, upon accurate knowledge of the acquisition scan geometry, the relative position of the x-ray source and detector for each projection. Uncertainties in the scan geometry can lead to artifacts and/or blurring in the reconstructed object. The development of portable tomosynthesis systems has been hampered by difficulties in accurately determining the acquisition scan geometry. There remains a need for improved X-ray tomosynthesis systems that can be made portable and still provide reliable clinical images and data.

FIG. 1 is a diagram that shows a perspective view of a mobile radiographic apparatus 100 that can use portable radiographic detectors or flat panel detectors according to embodiments of the application. The exemplary mobile x-ray or radiographic apparatus 100 of FIG. 1 can be employed for digital radiography (DR) and/or tomosynthesis. As shown in FIG. 1, mobile radiographic apparatus 100 can include a moveable transport frame 120 that includes a first display 110 and an optional second display 110' to display relevant information such as obtained images and related data. The second display 110' can be pivotably mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s). An optional touchpad 150 allows functions such as operator identification.

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the moveable transport frame 120) configured to retain at least one removable digital radiography (DR) detector. The storage area 130 can be configured to hold a plurality of detectors and can also be configured to hold one size or multiple sizes of DR detectors.

Mounted to the moveable transport frame 120 is a support column 135 that supports an x-ray source 140, also called an x-ray tube, tube head, or generator that can be mounted to the support column 135. In the embodiment shown in FIG. 1, the support member (e.g., support column 135) can include a second section that extends outward a fixed/variable distance from a first section where the second section is configured to ride vertically up and down the first section to the desired height for obtaining the image. In addition, the support column 135 is mounted to be rotatable with respect to the moveable transport frame 120. In another embodiment, the tube head or x-ray source 140 can be coupled to rotate about the support column 135. In another exemplary embodiment, an articulated member of the support column 135 that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

Figure 2:
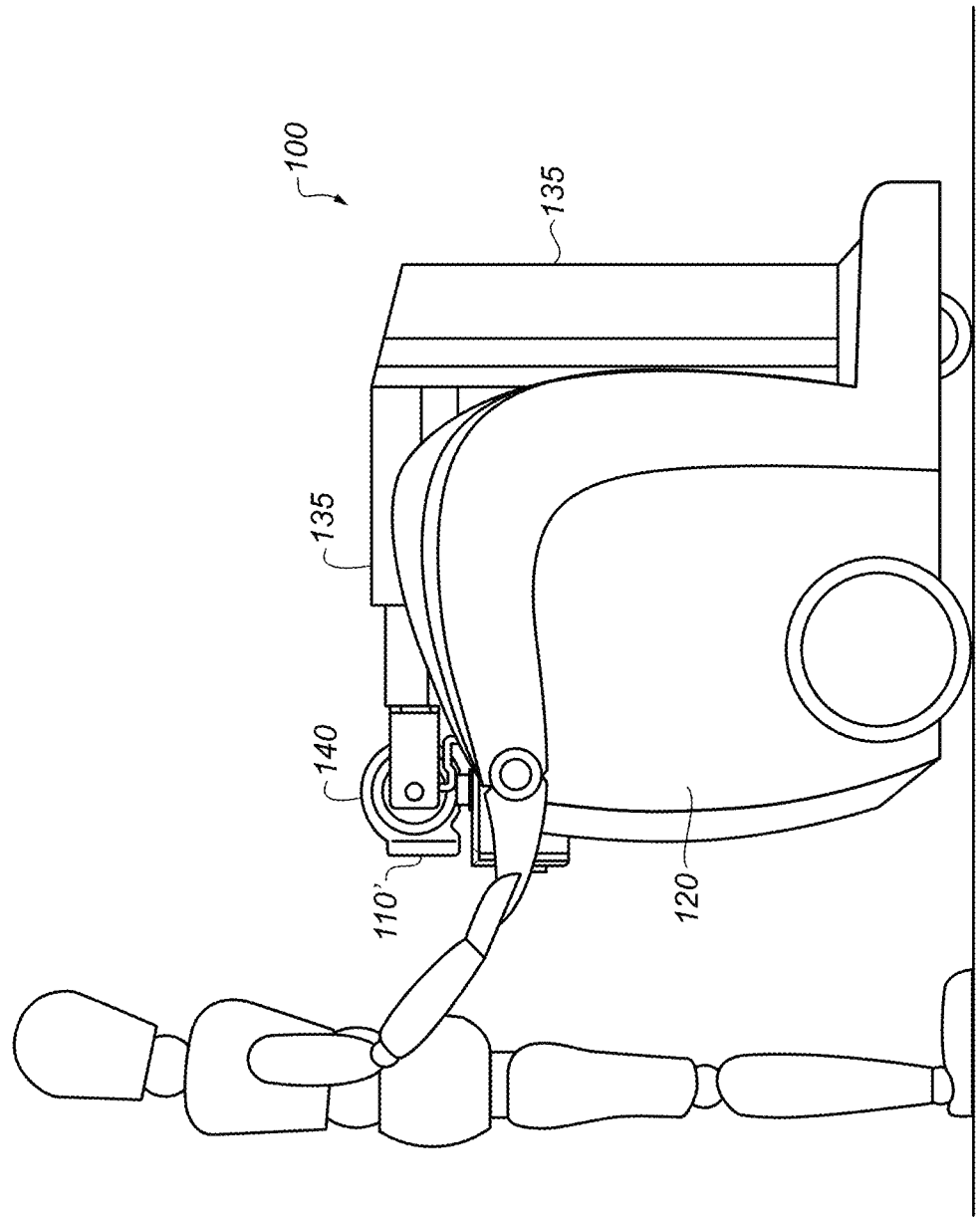
FIG. 2 is a diagram that shows a perspective view of a mobile radiography unit of FIG. 1 positioned for travel.

As shown in FIG. 2, for ease during transport of the mobile radiographic apparatus 100, the support column 135 and x-ray source 140 can be arranged to seat closely to the moveable transport frame 120. As shown in FIG. 2, the second display 110' can be in a viewable position (e.g., operable) during transport of the mobile radiographic apparatus 100. When the mobile radiographic apparatus 100 is to be used, the support column 135 and x-ray source 140 can be extended from the moveable transport frame 120 for proper positioning (e.g., by the operator, a user, or x-ray technician) and the second display 110' moved to viewable position such as shown in FIG. 1.

Figure 3:
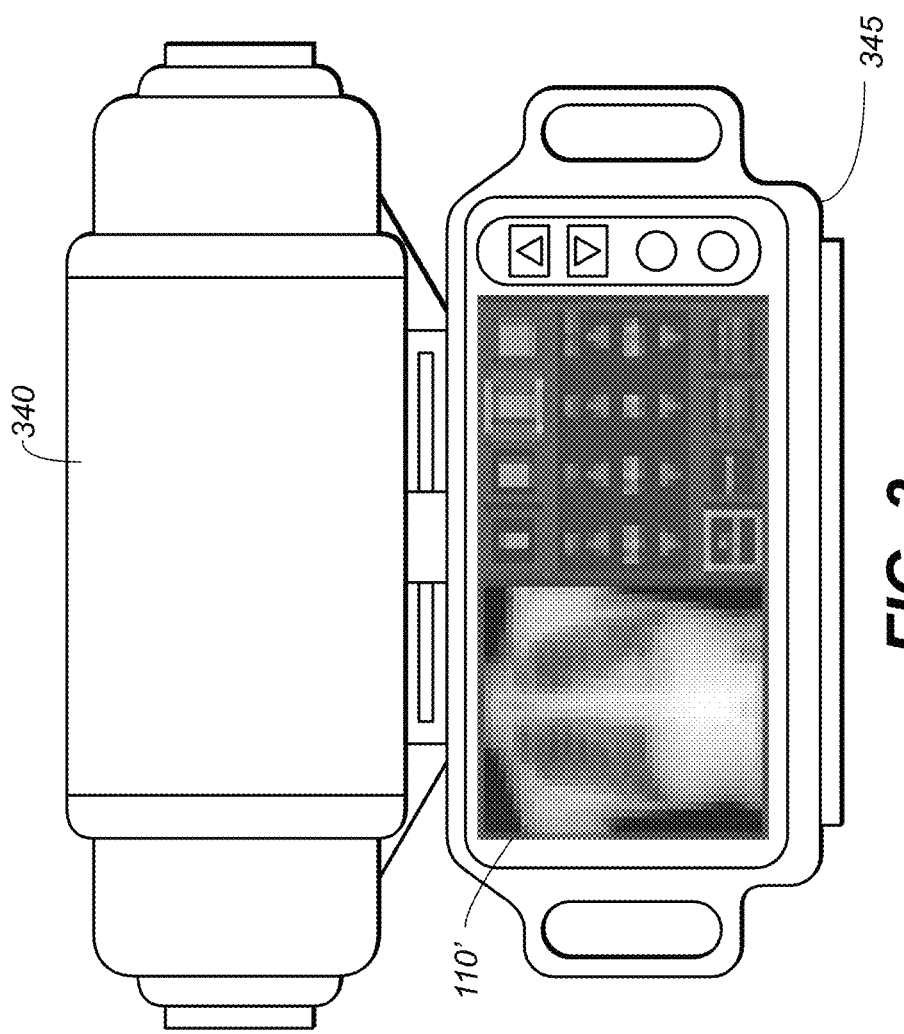
FIG. 3 is a diagram that shows an exemplary embodiment of a display/monitor as a second display mounted to a boom assembly of a mobile radiography unit according to the present disclosure.

FIG. 3 is a diagram that shows an exemplary embodiment of a display/monitor as a second display 110' mounted to a boom assembly of a mobile radiographic apparatus 100 according to the application. As shown in FIG. 3, the second display 110' can be mounted to a collimator 345 of an x-ray source 340 of a support column 135 of a mobile radiographic apparatus 100. In one embodiment, the collimator 345 can be mounted to rotate with respect to the x-ray source 340, so that the collimator 345 (e.g., second display 110') can swivel at least 90 degrees, at least 180 degrees or 360 degrees. As shown in FIG. 3, the second display 110' is coupled to a plurality of handles for ease of positioning. Alternatively, the second display 110' can be mounted (e.g., rotatably) to x-ray source 340 above a collimator 345 of a boom assembly of a mobile radiography unit.

Figure 4:
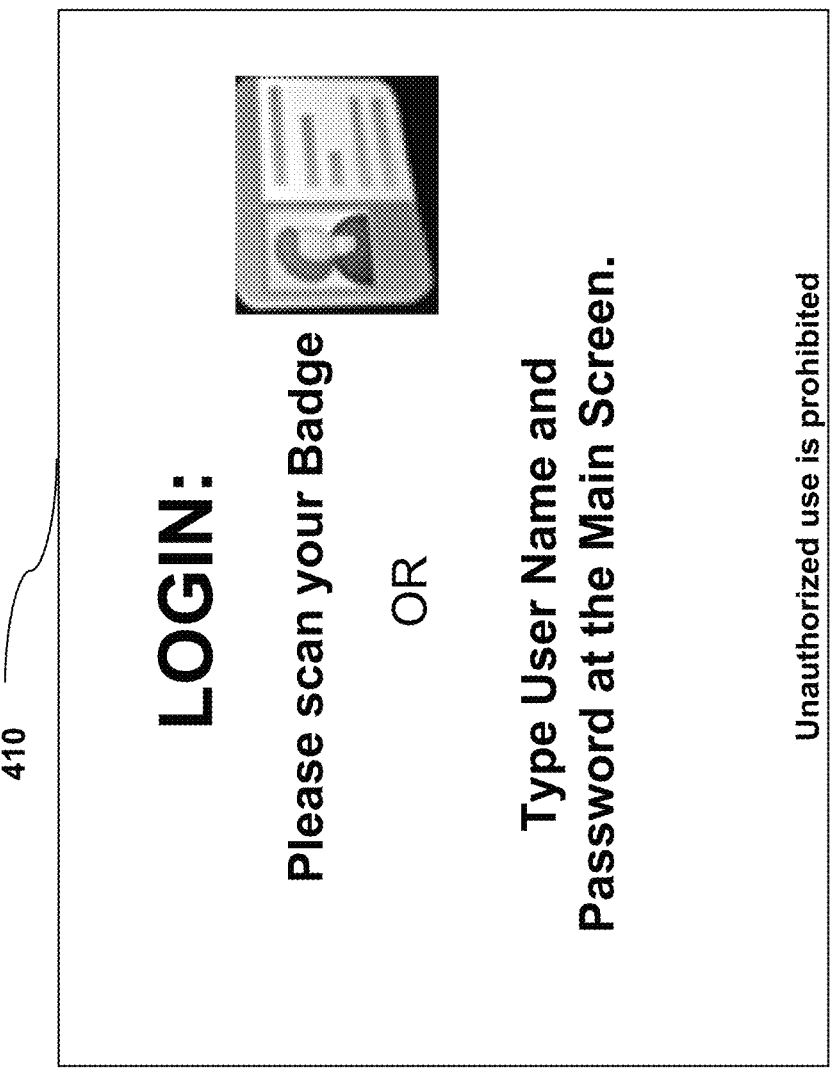
FIG. 4 is a diagram that illustrates an embodiment of a sign-on screen according to the present disclosure.

FIG. 4 is a diagram that illustrates an embodiment of a sign on screen according to the application. Thus, when an attempt is made to operate the mobile radiographic apparatus 100, a sign on screen 410 can be displayed to provide instructions to a user. As shown in FIG. 4, the single sign on screen 410 can provide instructions for sign on sign on and activate the mobile radiographic apparatus 100 such as "LOGIN: Please scan your badge or type User Name and Password at the main screen." Exemplary embodiments of a pass key or ID badge can include but are not intended to be limited to a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

According to embodiments of the application, the first display 110 and the second display 110' (FIG. 1) can provide capabilities/functionality to the mobile radiographic apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm the correct patient); (iv) display and/or change a Patient Worklist, such as a list of exams to perform and allow the user to select an exam. (In one embodiment, such a patient worklist can be automatically updated (e.g., synchronized to a master/hospital/doctor worklist) using a wired or wireless network/connection. In one embodiment, the mobile radiographic apparatus 100 can highlight/indicate new exams (e.g., on the second display 110') upon receipt of the scheduled examination.); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile radiographic apparatus 100 during transport, e.g., using a video camera located on the other side (e.g., front side of the mobile radiographic apparatus 100). In one embodiment, the mobile radiographic apparatus 100 can include a collision avoidance system with alerts (e.g., audible, visual), and automatic maneuvering to avoid unnecessary contact in the examining room (e.g., by stopping or course modification).

Figure 6:
Figure 7:
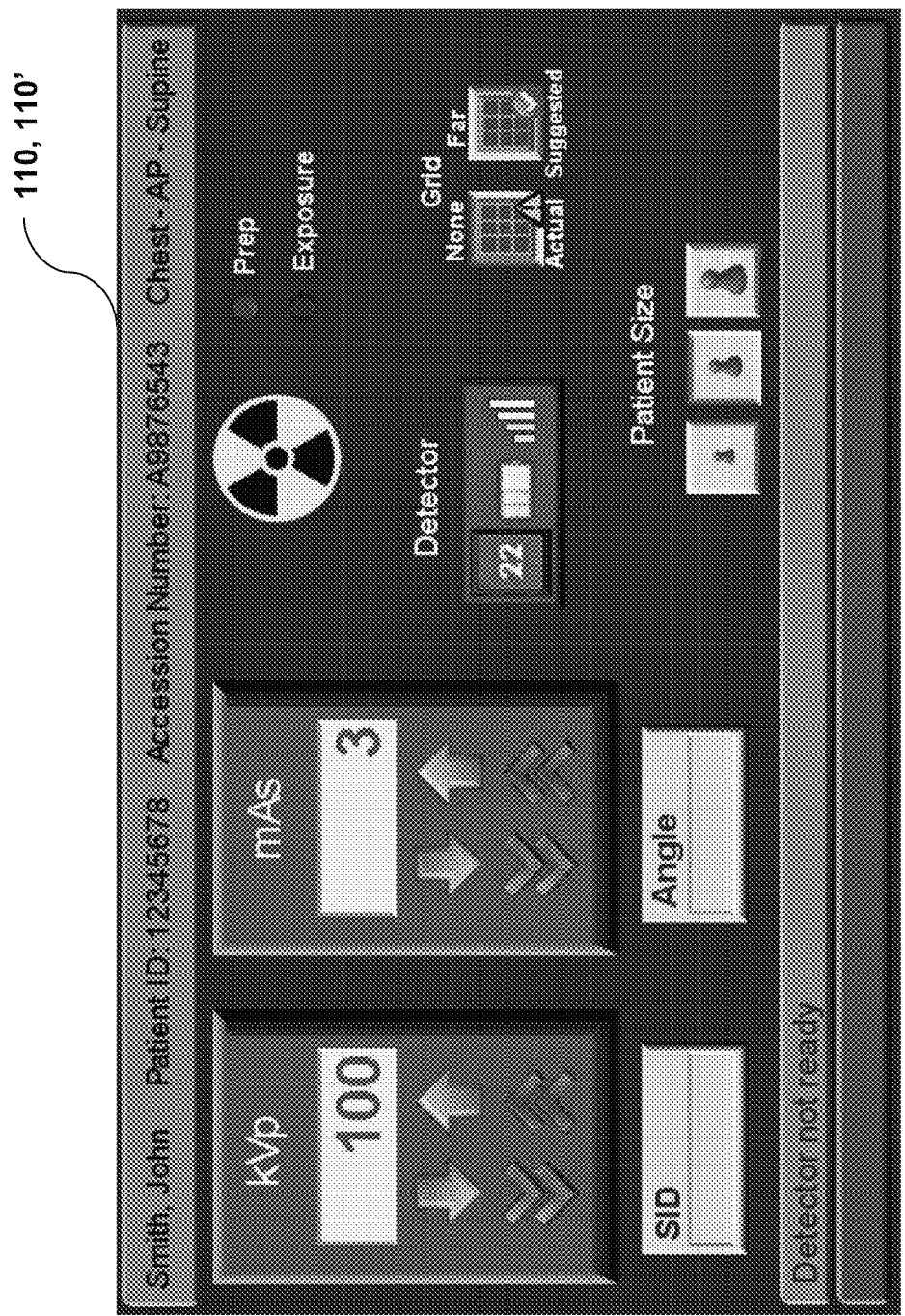
Figure 8:
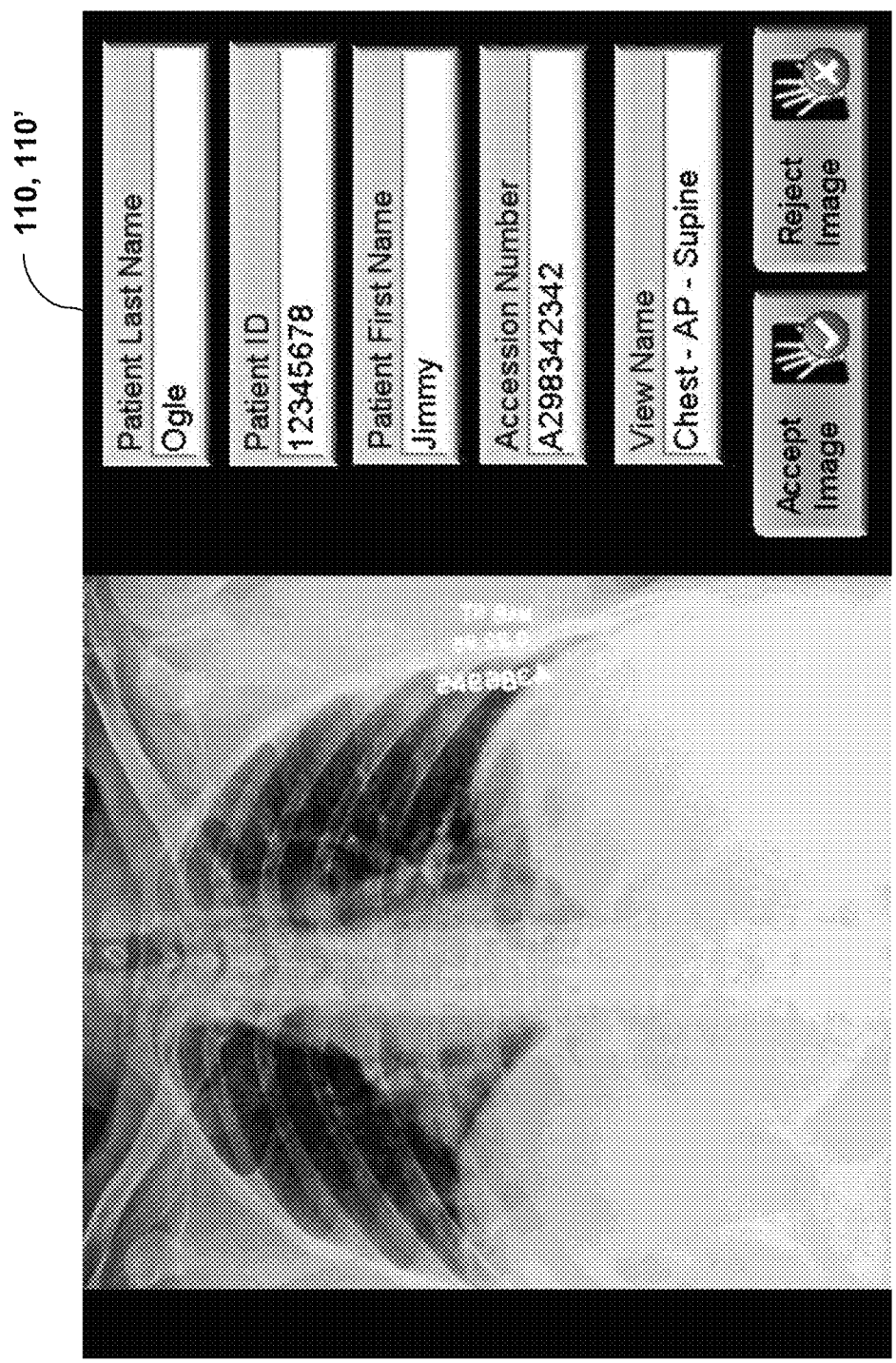

FIGS. 5-8 are diagrams that illustrate exemplary non-limiting representative functions illustrated on an embodiment of a second display of a mobile x-ray imaging apparatus as was shown in FIG. 1. As shown in FIG. 5, an example of a work list is shown on a monitor of the second display 110'. As shown in FIG. 6, an example of a new examination/procedure information/requirement for that technician and/or patient is shown on a monitor of the second display 110'. As shown in FIG. 7, an example of x-ray source controls is shown on a monitor of the second display 110'. As shown in FIG. 8, an example of newly acquired image and patient information is shown on a monitor of the second display 110'.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

Figure 9:
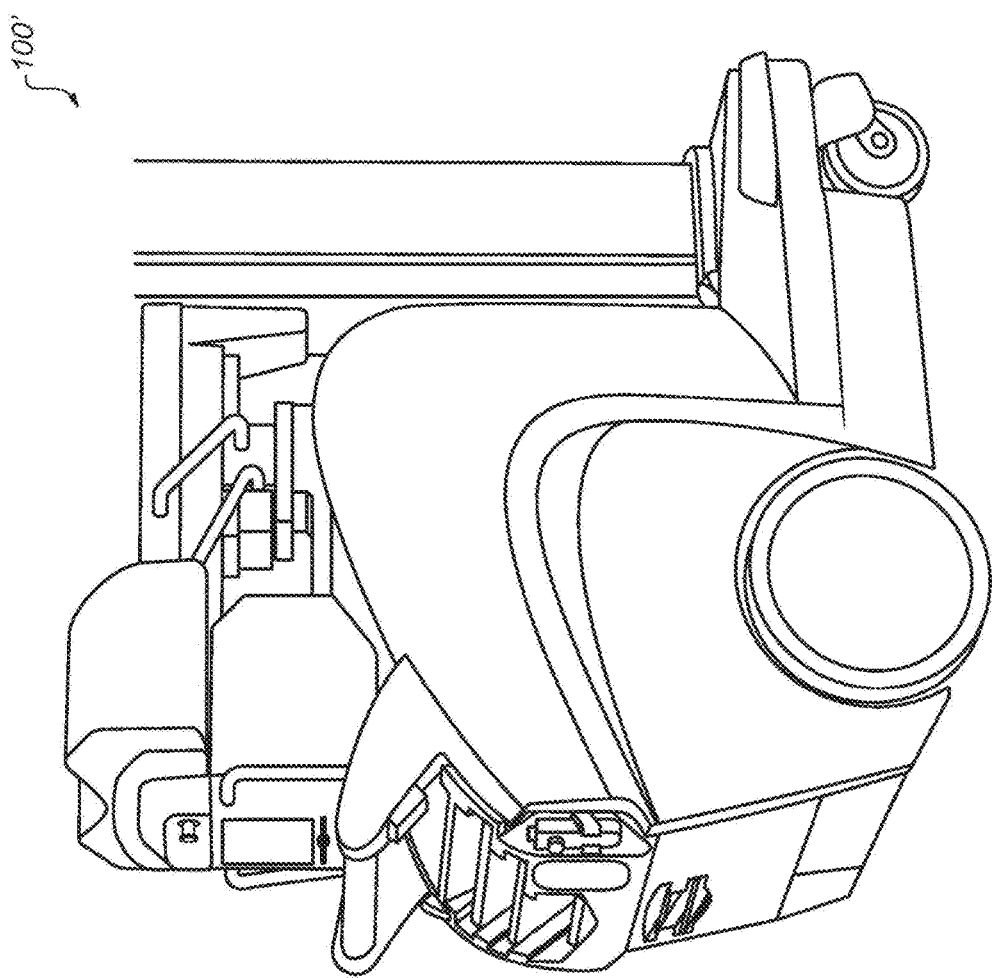
FIG. 9 is a diagram that shows a perspective view of a mobile radiography unit according to another embodiment of the application.

FIG. 9 is a diagram that shows a perspective view of a mobile radiography unit 100' according to another embodiment of the application.

Figure 10:
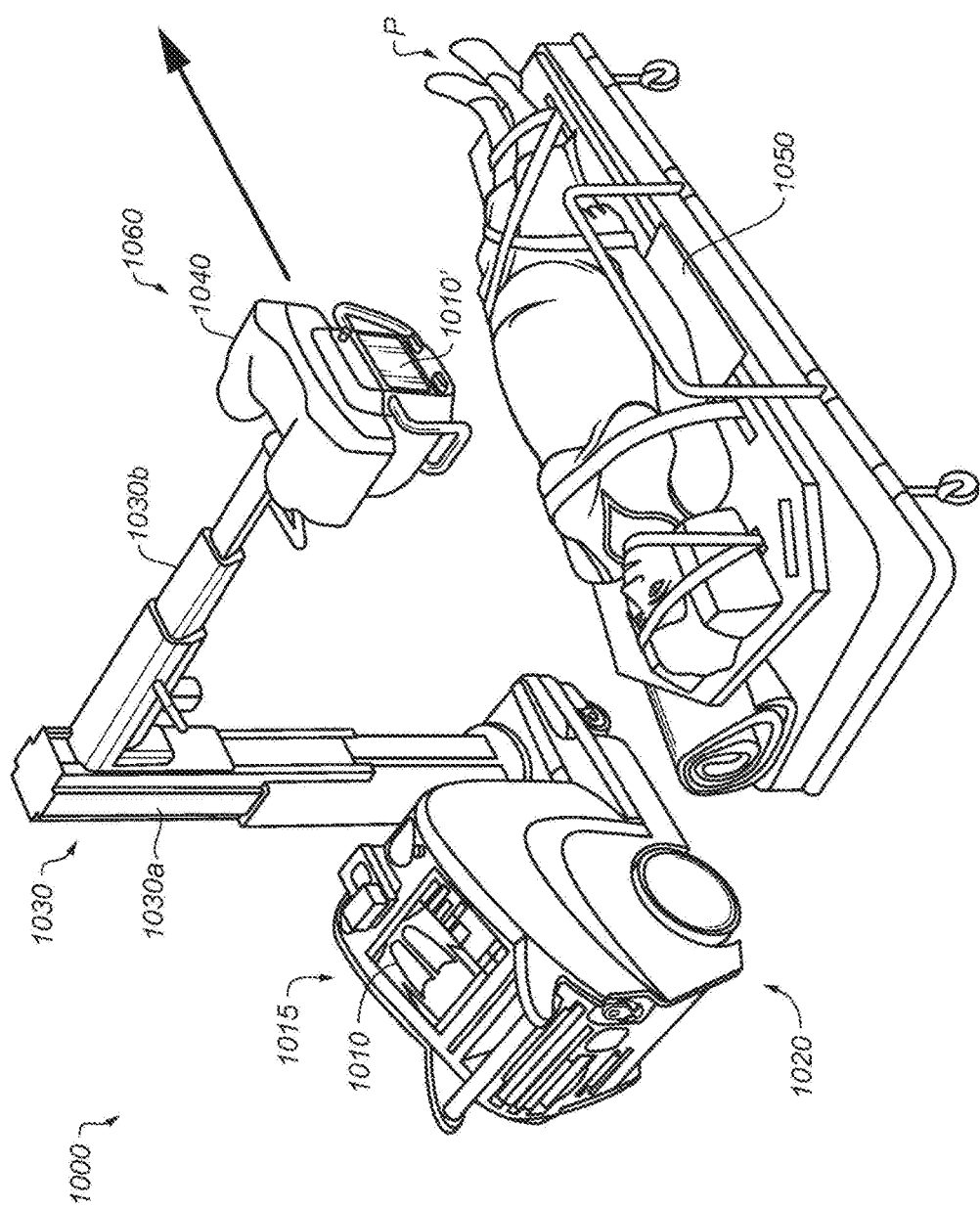
FIG. 10 is a diagram that shows a perspective view of a mobile radiography unit that can provide a tomosynthesis capability according to embodiments of the present disclosure.

FIG. 10 is a diagram that shows a perspective view of a mobile radiography unit that can provide a tomosynthesis capability according to embodiments of the application. In one embodiment, a mobile radiography unit can be a tomosynthesis system. As shown in FIG. 10, an embodiment of a portable tomosynthesis system 1000 is shown that can include a movable transport frame 1020. Mounted to the moveable transport frame 1020 can be a support column that supports an x-ray source 1040 as part of an x-ray source assembly 1060. As shown in FIG. 10, a support column 1030 can include a second section 1030*b* that extends outward a fixed/variable distance from a first section 1030*a* where the second section 1030*b* is configured to ride vertically up and down the first section 1030*a* to the desired height for obtaining the projection images. The system also includes a digital x-ray detector 1050 that is wirelessly or by wire connected to a system controller 1015 contained inside the moveable transport frame 1020. The system controller 1015 can implement and/or control the functionality of the mobile radiographic unit 1000 (e.g., functionality provided through the displays 100, 100'). The system controller 1015 can be provided though one or more of a conventional general purpose processor, digital computer, microprocessor, RISC processor, signal processor, CPU, arithmetic logic unit (ALU), video digital signal processor (VDSP) and/or similar computational machines, programmed according to the teachings of the application, as will be apparent to those skilled in the relevant art(s).

The x-ray source 1040 can use a collimator to form beams that are directed towards the detector 1050. The x-ray source 1040 may also include positioning, such as motors, which allow for directing the beam towards the detector. The moveable transport frame 1020 can include a first display 1010 and the x-ray source 1040 can be coupled to a second optional display 1010'. The system controller 1015 can coordinate operations of the x-ray source 1040, detector 1050, and moveable transport frame 1020. The system controller 1015 can control operations of the x-ray source, which may include the collimator, positioning devices and triggering of image acquisition by emission of x-rays from the source. The system controller 1015 also can control operations of the detector 1050, which may include triggering of the image acquisition and transmission of the acquired images back to the controller. In addition, the system controller 1015 can control the movement of the transport frame 1020.

FIG. 10 shows an embodiment of a portable tomosynthesis system where the x-ray source 1040 assembly can be moved along a prescribed path relative to the detector 1050 or relative to geometry of the detector 1050 and/or a patient (object) to be imaged. As shown in FIG. 10, the moveable transport frame 1020 can move the x-ray source 1040 assembly along a prescribed path (e.g., linear/non-linear motion) illustrated by an arrow.

Figure 11A:
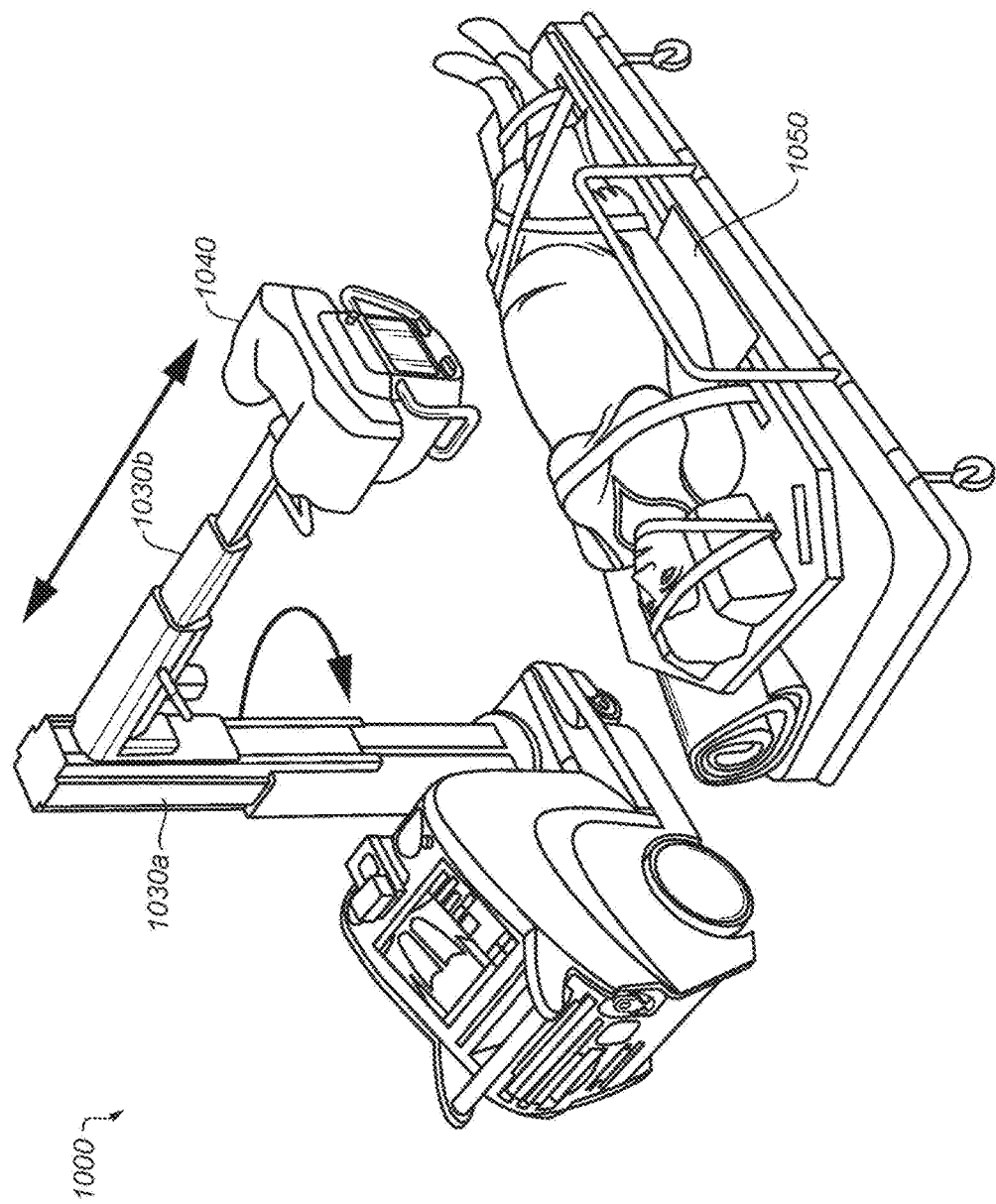
FIGS. 11A-11B are diagrams that show perspective views of alternative mobile radiography units that can provide a tomosynthesis capability according to embodiments of the present disclosure.
Figure 11B:
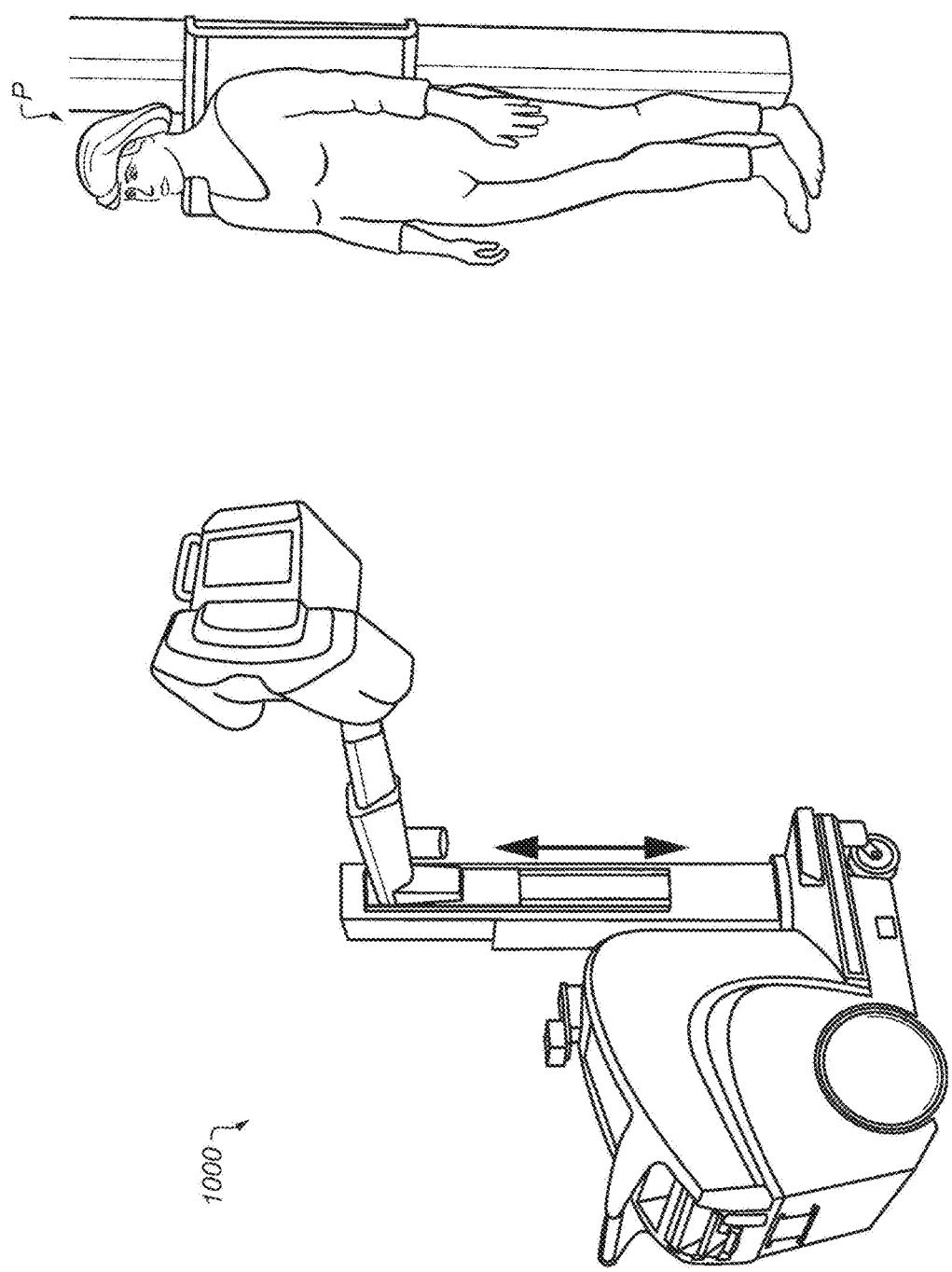

FIGS. 11A-11B are diagrams that show perspective views of additional mobile radiography units that can provide tomosynthesis capabilities according to embodiments of the application. As shown in FIG. 11A, the support column 1030 can move the x-ray source 1040 assembly along a prescribed path (e.g., linear/non-linear, curved, 2D or 3D) illustrated by an arrows. In certain exemplary embodiments, the second section 1030*b* and/or the first section 1030*a* can independently move the x-ray source 1040 assembly or move the x-ray source 1040 assembly in combination (e.g., concurrently). Further, the moveable transport frame 1020 can move the x-ray source 1040 assembly in combination with the support column 1030. In one embodiment, the mobile radiography units can include a tomosynthesis capability for a patient P as shown in FIG. 11B can further be used for LLI (Long Length Imaging).

Figure 12:
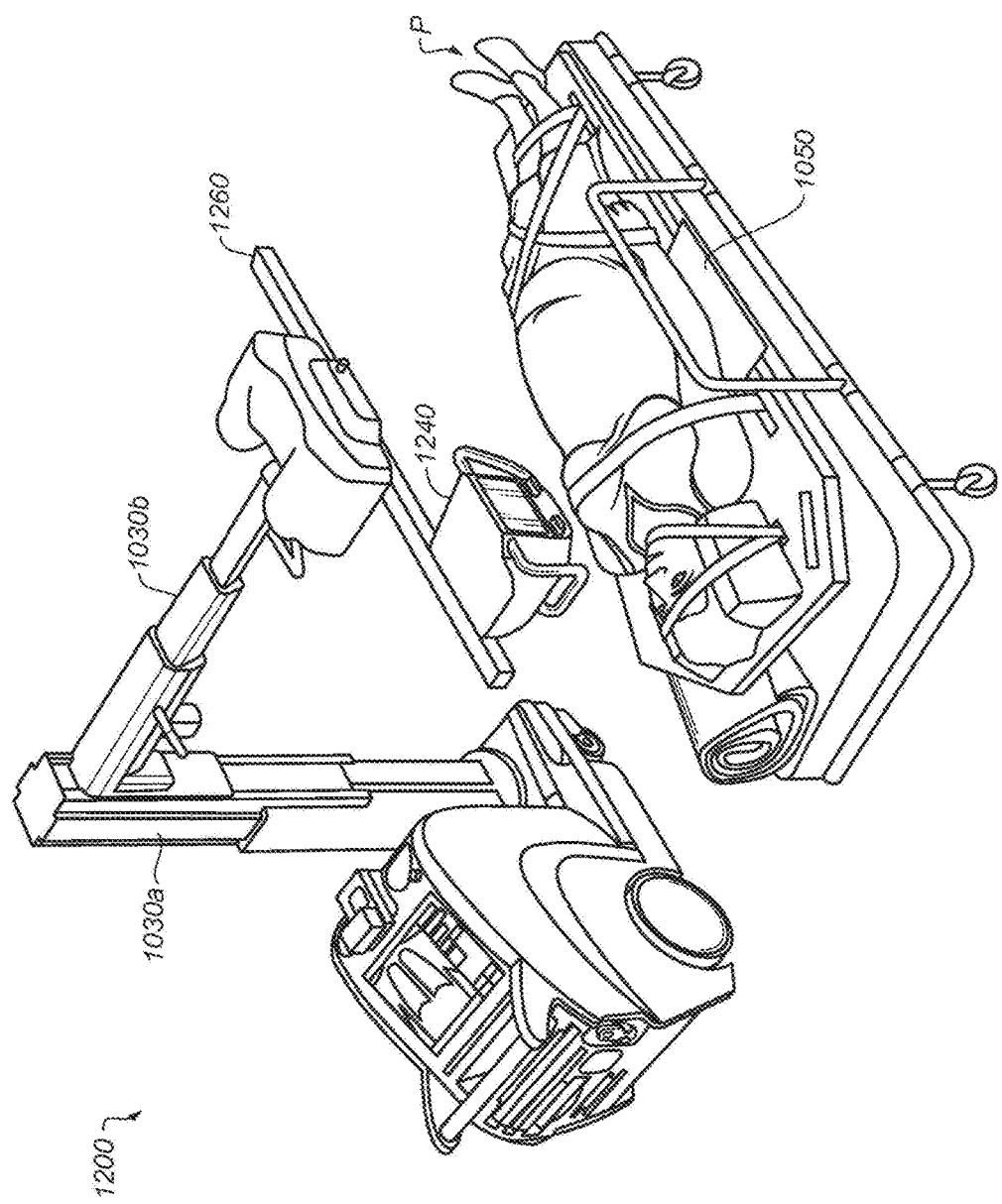
FIG. 12 is a diagram that shows a perspective view of another mobile radiography unit that can provide a tomosynthesis capability according to embodiments of the present disclosure.

FIG. 12 is a diagram that shows a perspective view of another mobile radiography unit 1200 that can provide a tomosynthesis capability according to embodiments of the application. In one embodiment of a portable tomosynthesis system, an x-ray source assembly can be configured to move along a prescribed path (e.g., linear path). FIG. 12 shows an embodiment of a portable tomosynthesis system where the x-ray source assembly is replaced by an X-ray source 1240 designed to move along a linear path on a support track 1260.

Figure 13:
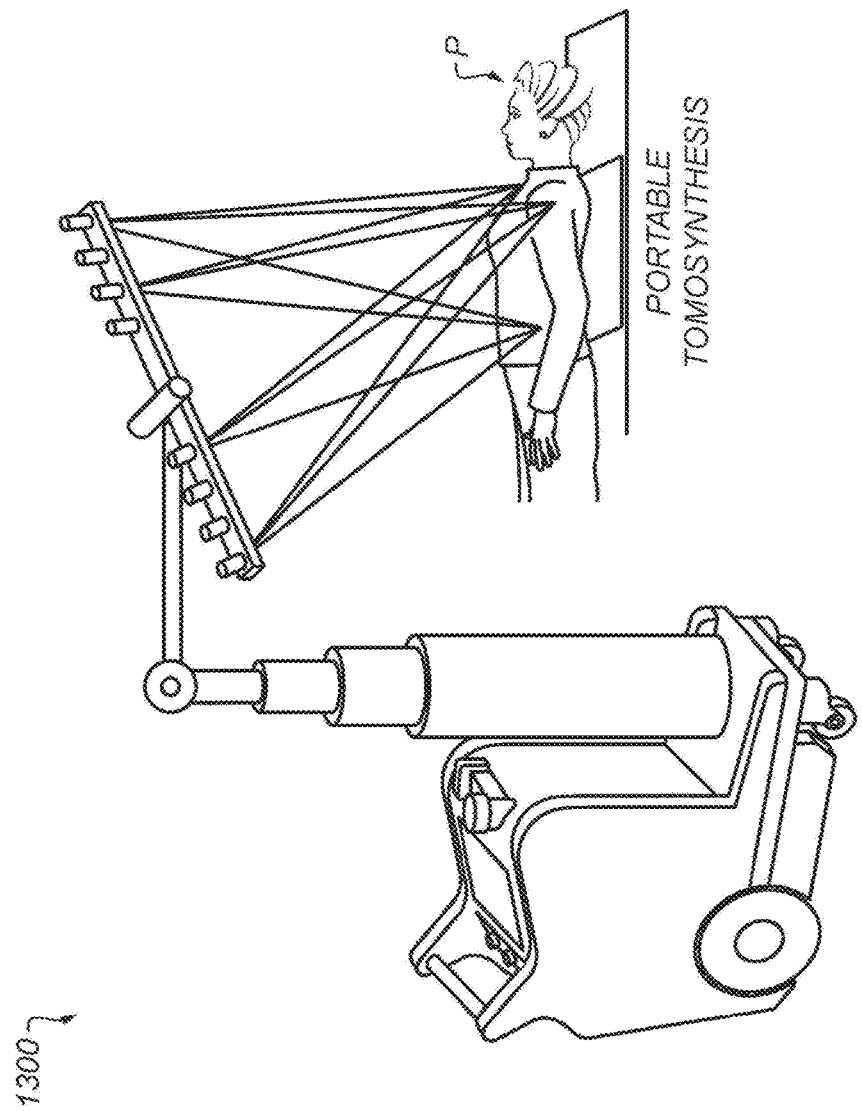
FIG. 13 is a diagram that shows a perspective view of yet another mobile radiography unit that can provide a tomosynthesis capability according to embodiments of the present disclosure.

FIG. 13 is a diagram that shows a perspective view of another mobile radiography unit 1300 that can provide a tomosynthesis capability according to embodiments of the application. In certain exemplary embodiments of portable tomosynthesis systems, the moveable mounted x-ray source can be replaced by a plurality of multiple individually controlled x-rays sources. FIG. 13 shows an embodiment of a portable tomosynthesis system where the multiple individually controlled x-rays sources are distributed sources (e.g., linearly distributed). The distributed sources can be arrayed in a prescribed spatial relationship.

Figure 14:
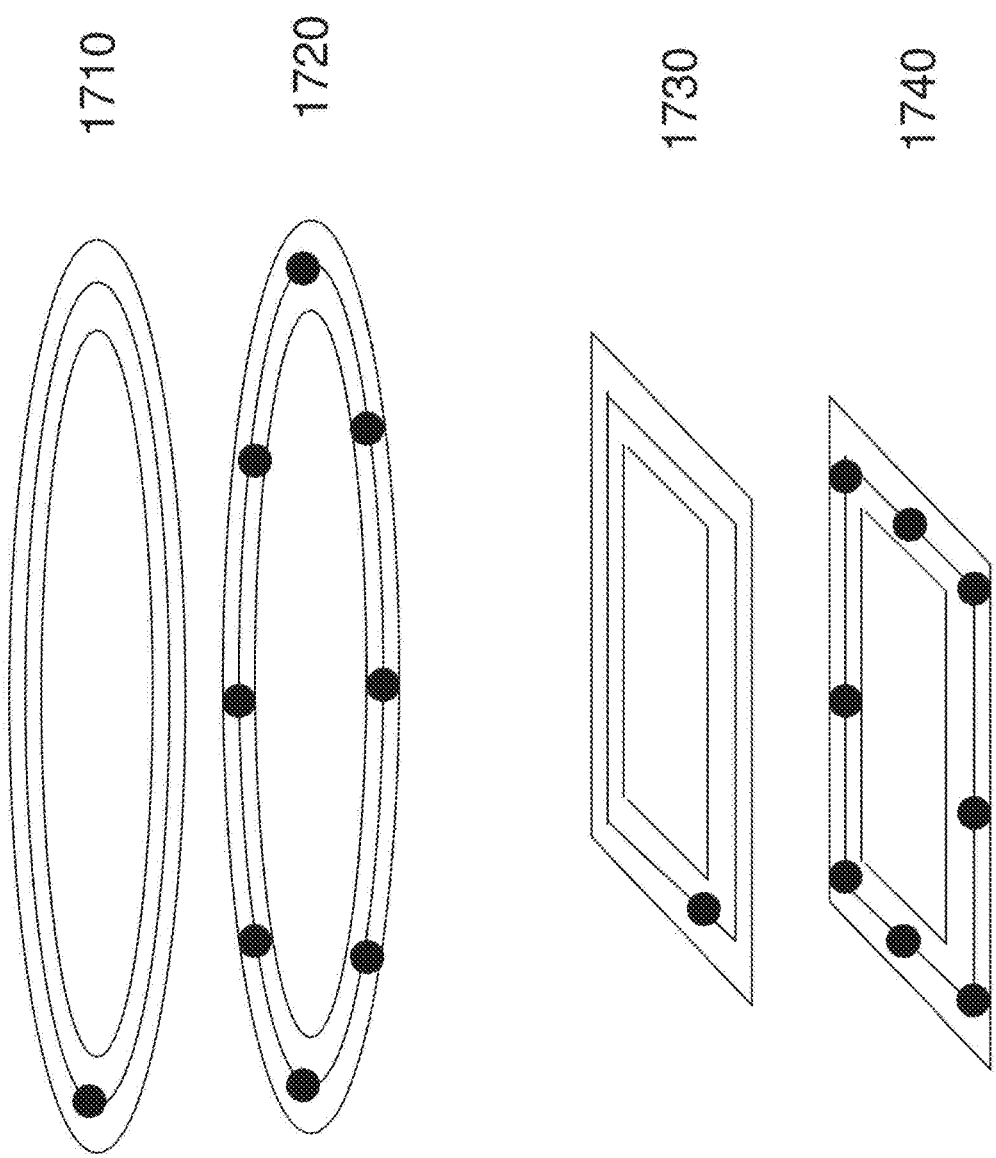
FIG. 14 is a diagram that shows examples of non-linear x-ray scan paths according to embodiments of the present disclosure.

Alternatively, different x-ray source paths can be used to modify or address reconstruction artifacts that can be caused by limited angular scanning systems such as radiographic tomosynthesis imaging systems. In addition, various x-ray scan paths can be used to accentuate the desired imaged structures and/or reduce or minimize artifacts that might confound or mask the ability to make an accurate diagnosis. FIG. 14 is a diagram that shows examples of non-linear x-ray scan paths (e.g., circular and square paths). In one embodiment, the moveable x-ray source is mounted on a circular 1710 (square 1730) track or a plurality of sources are spatially distributed in a circular 1720 (square 1740) pattern. However, embodiments of the application are not intended to be so limited, for example other non-linear, curved, 2D or 3D scan paths or movable x-ray supports can be used. Further, source assemblies can be used to ensure that radiation emitted by the moveable or distributed x-ray source is directed towards the detector (e.g., through the object/patient). In one embodiment, the source assemblies can include adjustable collimators (e.g., before or during an image acquisition scan). In one embodiment, the adjustable collimators can be individually and/or concurrently moved.

In one embodiment, a mobile radiographic imaging system is intended to support critically ill patients in an ICU that are currently transported out of ICU for x-ray imaging. For example, ICU patients can receive a tomosynthesis procedure; otherwise, these patients might need to be transported out of ICU in order to obtain a CT exam. For example, CT imaging is often needed for ICU patients in order to differentiate various types of fluids induced by plural effusions, such as blood, water, and the like, so that corrective actions can be taken. However, transporting ICU patients to the CT exam area can be a challenging task due to their severe clinical conditions. Further, visualization software can be provided to facilitate interpretation of ICU-related chest abnormalities. For instance, presentation of the low exposure sequences (prior to reconstruction of the slide data) may allow the ICU physician to "look around" rib structures and the like.

As is shown schematically in the arrangements of FIGS. 10-13, the x-ray detector is positionally uncoupled from the x-ray source. Alternately stated, the detector and source are mechanically uncoupled; there is no mechanically fixed spatial arrangement for source-detector positioning. The operator attempts to approximate an appropriate angular and distance relationship between the source and detector; however, this relationship is at best, a close approximation of a recommended distance for the patient anatomy being imaged.

Figure 15:
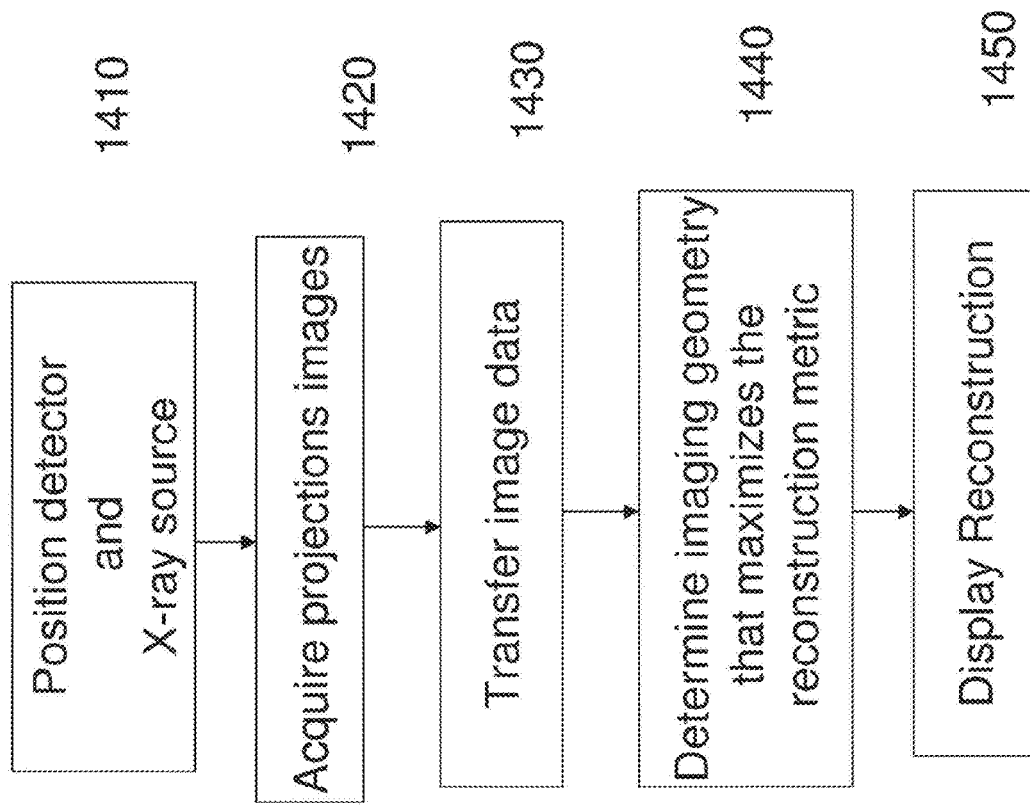
FIG. 15 is a flow chart that shows an exemplary method of operating exemplary mobile radiographic imaging systems for acquiring projection images and generating reconstructions of (e.g., three-dimensional) tomosynthesis images according to embodiments of the present disclosure.

Referring to FIG. 15, a flow chart shows an exemplary method of acquiring projections images and generating the reconstruction of three-dimensional tomosynthesis images. The method for acquiring projection images and generating the reconstruction of three-dimensional tomosynthesis images will be described using embodiments of mobile radiography apparatus shown in FIGS. 10-13 and can be applied to mobile x-ray systems/carts shown in FIGS. 1 and 10-13; however, the method of FIG. 15 is not intended to be limited thereby.

As shown in FIG. 15, the detector and x-ray source can be positioned (operation block 1410). For example, the x-ray source can be moved to its initial position and the detector can be positioned such that the patient P is interposed between the detector and x-ray source.

For exemplary portable tomosynthesis system embodiments 1000, 1200, 1300, the initial x-ray source assembly position can be set by the location of the transport frame and the support column. The height, extent and rotation positioning of the support column's first section 1030a and the second section 1030b can be used to position the x-ray source assembly to the initial desired location above the patient the patient. Alternatively, the support (e.g., support 1260, track 1710, track 1730) and the location of the transport frame and/or the support column can set the initial x-ray source assembly position.

Then, a series of projections image can be acquired at different x-ray source positions (operation block 1420). In embodiment 1000, the projection images can be acquired while the transport frame, and thus attached x-ray source, is moved along a linear or non-linear path. In embodiment 1000, the projection images can be acquired while the height, extent, and rotation of the support columns first and second section are modulated so that the attached x-ray source, is moved along a linear or non-linear path. In embodiment 1200 of FIG. 12, the projection images can be acquired while the x-ray source is moved along the support track. In embodiment 1300 of FIG. 13, the projection images can be acquired while individual x-ray sources are triggered.

Then, following the sequence of FIG. 15, the acquired projection image data can be received (e.g., transfer back from the detector to) by control and processing components of the system controller (operation block 1430). The projection images can be displayed on display 110 and/or undergo a quality check (e.g., automated or by the operator) before being further processed. The imaging geometry that corresponds to a predetermined reconstruction metric, such as an image quality metric related to gradient, histogram, or entropy of the reconstructed object, is determined in an operation block 1440.

Then, the reconstruction volume can be displayed on display 110, 110' (operation block 1450) and/or undergo a quality check before storing the volume. In one embodiment, the reconstruction volume can be stored after the quality check (e.g., before display thereof).

An example of a data fidelity metric is:

$$E_5 = \frac{1}{2} \sum_{i=1}^{nProjs} \|A_i f - p_i\|^2$$

or a regularized version, $$E_6 = R(f) + \frac{1}{2} \sum_{i=1}^{nProjs} \|A_i f - p_i\|^2$$

wherein $A_i$ is the projection matrix for the ith projection, f and p are vector representations of the reconstruction volume and projection images, and R( ) is a regularizer imposing a prior, such as smoothness, on the reconstruction f. The projection matrices A are a function of the imaging geometry.

The image quality of the reconstruction depends, in part, upon the accurate knowledge of the position of the x-ray source and detector for each projection. Uncertainties in the scan geometry can lead to artifacts and/or blurring in the reconstruction. Further, accurate positioning of the detector using a grid can be desirable or fundamental to allow impinging x-rays to pass the grid to reach, in whole or in part, the detector. For a portable stationary detector tomosynthesis system, the scan geometry can correspond to the set x-ray source locations relative to the stationary detector. The position encoders associated with the moveable frame and moveable x-ray source assembly can provide accurate information about the spatial location of the x-ray source in a local coordinate system associated with the x-ray source assembly. For a distributed source assembly, the spatial location of x-ray sources can be fixed in the local coordinate system. For the portable tomosynthesis system, the detector and x-ray source are physically separated from each other. As a consequence, the relative orientation and distance between the x-ray source assembly and the detector local coordinate systems are not fixed or accurately known beforehand. In one exemplary embodiment, a detector can be physically separated and tethered to the portable tomosynthesis system, however, such system geometry (e.g., position, orientation etc. of detector, x-ray source(s)) can be unknown.

Figure 16:
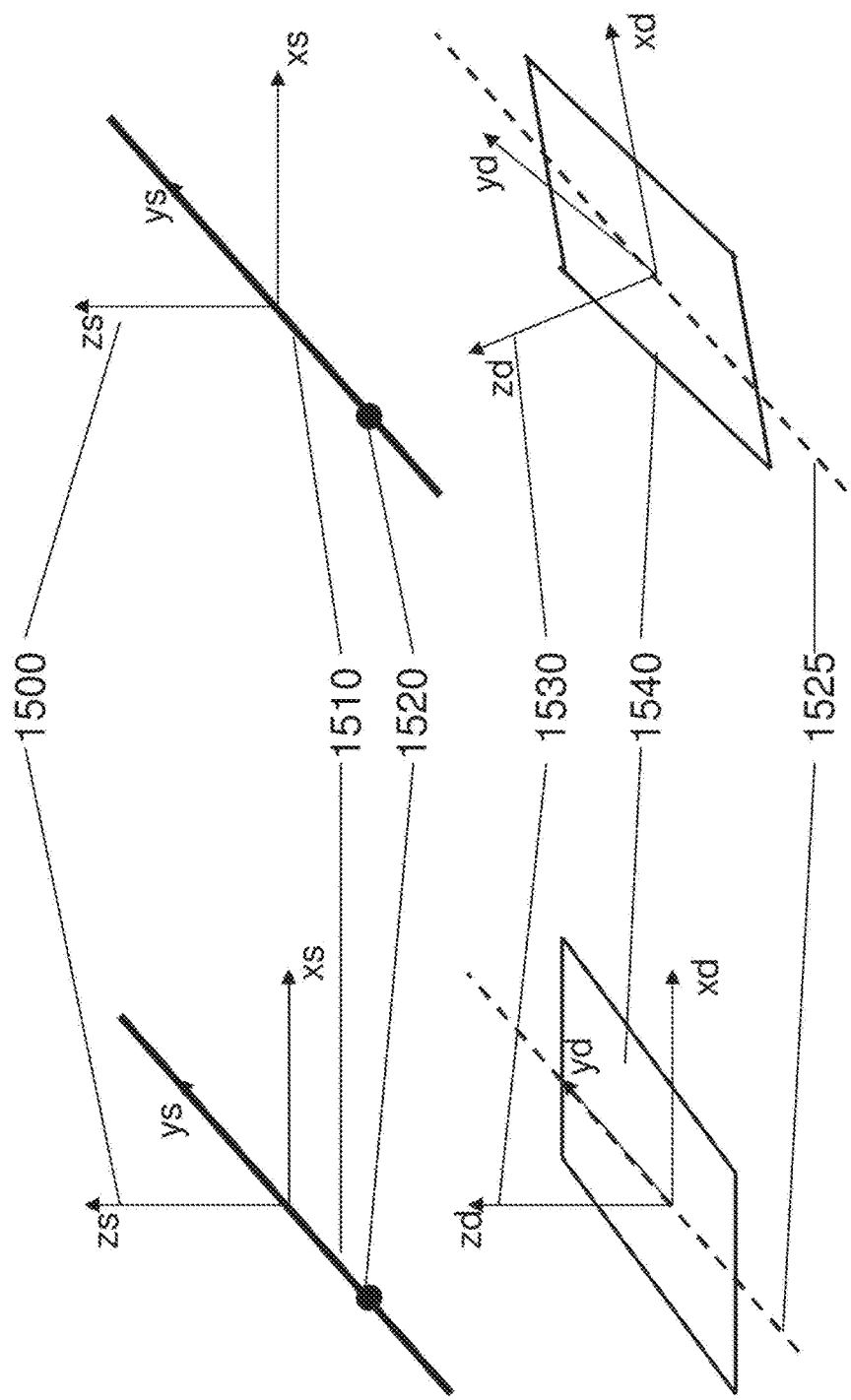
FIG. 16 shows diagrams that schematically show exemplary relative orientation and distance between an x-ray source coordinate system and a detector coordinate system for a linear scan tomosynthesis system according to embodiments of the present disclosure.

FIG. 16 is a schematic diagram that shows exemplary relative orientation and distance between x-ray source coordinate system 1500 with coordinates ($x_s$, $y_s$, $z_s$) and the detector coordinate system 1530 with coordinates ($x_d$, $y_d$, $z_d$) for a linear scan tomosynthesis system. At left, FIG. 16 shows a desired aligned tomosynthesis system (e.g., selected alignment or ideally aligned), where the detector and x-ray source coordinates have the same orientation. A projection 1525 of the trajectory 1510 of the x-ray source 1520 onto the detector 1540 is aligned with the one of the detector's in-plane axes and the distance between the x-ray source and detector along the x-ray source's trajectory is constant.

At the right, FIG. 16 shows a system where the detector and x-ray source coordinates have different orientations so that, as a result, the distance of the x-ray source to the detector plane now varies along the x-ray source trajectory. As was shown in FIG. 12, this type of mismatch in orientation between the x-ray source assembly 1060 and detector 1050 can occur when the detector 1050 is placed under a bedridden patient.

Figure 17:
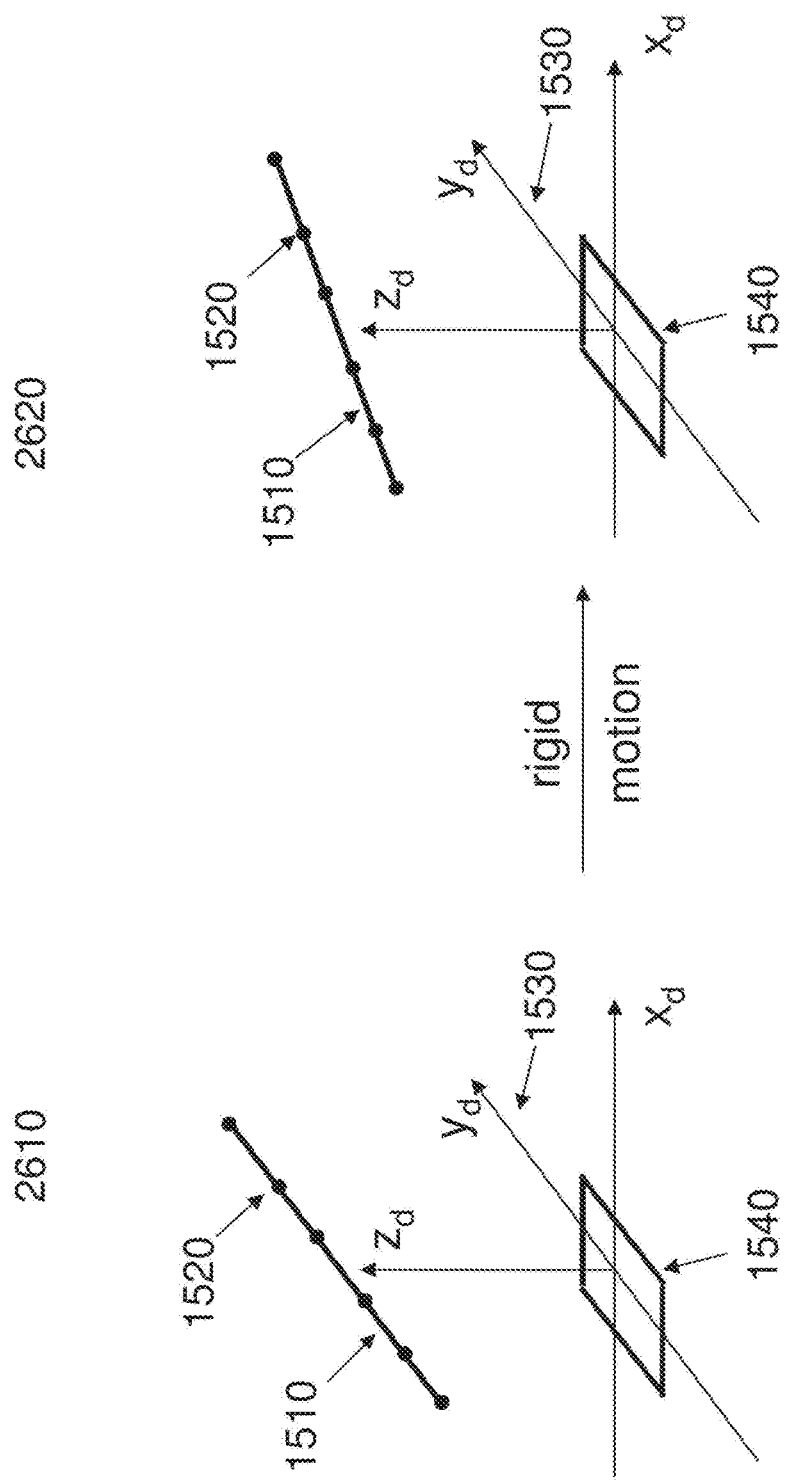
FIG. 17 is a diagram that schematically shows an exemplary resulting orientation and distance of a linear track x-ray source assembly after applying rigid motion to a starting orientation and distance of a linear track x-ray source assembly according to embodiments of the present disclosure.

The imaging parameters can be the set or some subset of x-ray source locations $\{xs_i, ys_i, zs_i\}$ relative to the stationary detector for each projection image used in the reconstruction. Alternatively, if the distances between the x-ray source locations are known, as described above, then the imaging parameters correspond to the relative orientation and distance between the x-ray source assembly and the detector. This corresponds to determining the set or subset of rigid motion parameters that convert the assumed nominal x-ray source positions to positions in space that optimize the reconstruction metric. FIG. 17 is a diagram that shows an exemplary resulting orientation and distance of a linear track x-ray source assembly 2620 after applying rigid motion to the starting orientation and distance of a linear track x-ray source assembly 2610. The set rigid motion parameters can be the rotations θ, θy, θz along the detector's $x_d$, $y_d$, and $z_d$ axes.

Figure 18:
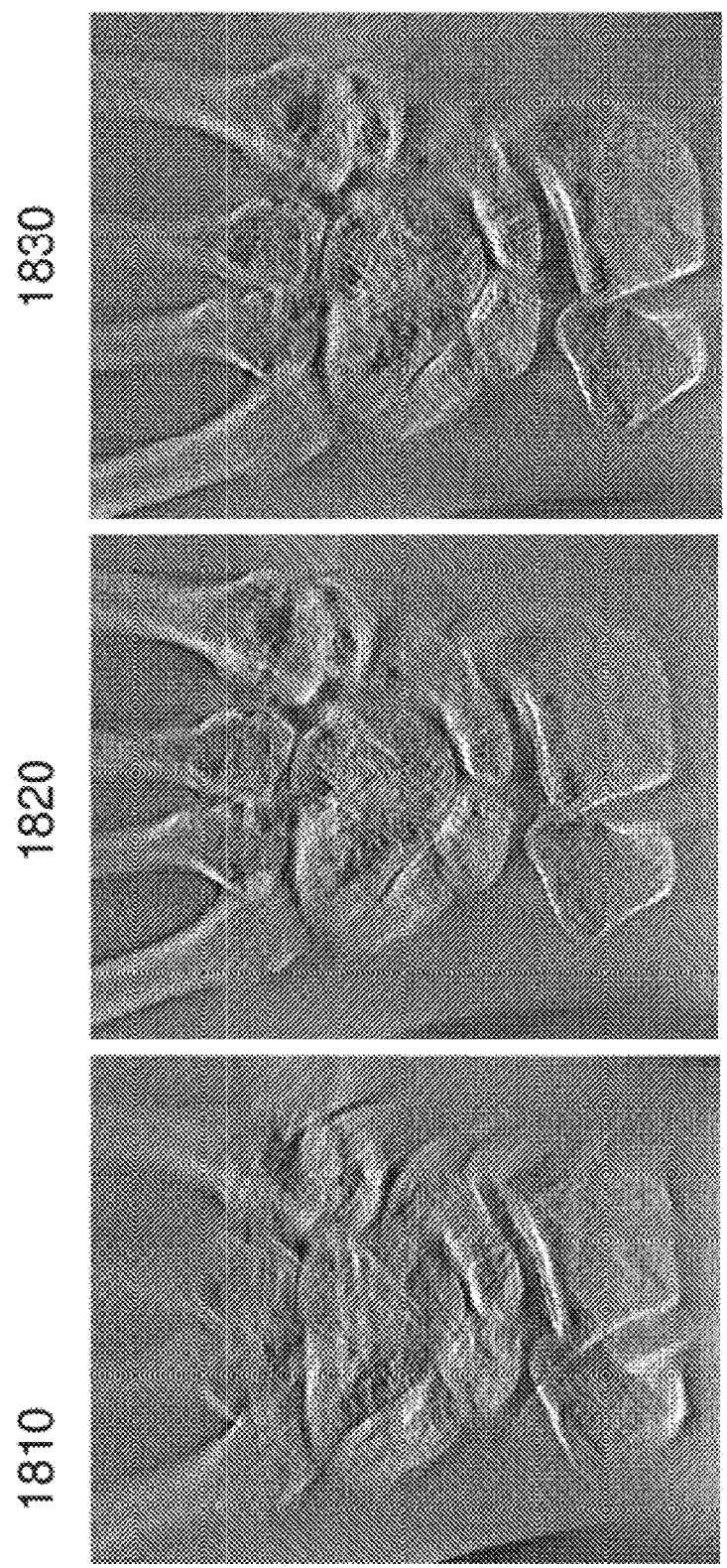
FIG. 18 is a diagram that shows a slice of the tomosynthesis reconstruction for an exemplary linear track scan using an assumed imaging geometry, a modified geometry as determined using imaging geometry auto-correction reconstruction, and an actual imaging geometry according to embodiments of the present disclosure.

FIG. 18 is a diagram that shows a slice of the tomosynthesis reconstruction for a linear track scan of a hand phantom using the assumed imaging geometry 1810, the optimized geometry 1820 as determined by an imaging geometry auto-correction reconstruction algorithm, and the actual imaging geometry 1830. For the assumed geometry the x-ray source assembly is translated 180 cm along the detector's z axis and has the same orientation as the detector. The actual geometry corresponds to the linear track being rotated −3.9 degree about its x axis followed by a −3.9 degree rotation about its z axis from its assumed position. As shown in FIG. 18, tomosynthesis reconstruction results using the imaging geometry calculated from the auto-correction reconstruction algorithm and the actual imaging geometry are essentially indistinguishable.

Various exemplary embodiments described herein can illustrate individual modes of operation. In certain exemplary embodiments, more than one mode can be provided in/by a single mobile radiographic imaging system and/or methods for using the same.

Certain exemplary embodiments of mobile radiographic imaging systems and/or methods for using the same can determine or use auto-correction reconstruction processes that can produce data in a unified coordinate system, for each image in a capture sequence that provides the relative x-ray source focal spot position and detector position and orientation. This information can have various multiple uses in tomosynthesis image reconstruction. For example, such information can be used in conjunction with X-ray exposure technique technical factors to estimate the signal the detector would receive with an "air exposure" (e.g., without any object/subject interposed between the source(s) and the detector). This "air exposure" image can be used in tomosynthesis reconstruction to provide the estimated linear attenuation coefficients for volumetric reconstruction processing. Further, a recovered geometry according to the application can also be used to apply tomosynthesis reconstruction approaches employing other methods such as SIRT (Simultaneous Iterative Reconstruction Technique), SART (Simultaneous Algebraic Reconstruction Technique), ART (Algebraic Reconstruction Technique) or other methods known by those skilled in the art of volumetric reconstruction algorithms. In addition, recovered geometry can also be used in patient dose estimation.

FIG. 19 is a diagram that shows a mobile radiographic imaging system that can include first and second (e.g., multiple) radiographic x-ray sources. As shown in FIG. 19, a mobile radiographic imaging system can include a first radiographic x-ray source and collimator, and a second x-ray source comprising a distributed source (e.g., rectangle) that can be either permanently attached or attached (detachable) when needed.

FIG. 20 is a diagram that shows a mobile radiographic imaging system that can include first and second (e.g., multiple) radiographic x-ray sources. As shown in FIG. 20, a mobile radiographic imaging system can include a first radiographic x-ray source and collimator, and a second x-ray source comprising a distributed source attachment (e.g., linear) that can be either permanently attached or attached (detachable) when needed. In one embodiment, the distributed sources can be on a curved support to maintain a single distance from a corresponding point on a detector. Exemplary distributed source attachment can have a first position for use and a second position for storage (e.g., folded) when not used. In one embodiment, exemplary distributed source attachments can have a first position for use, at least one intermediate position (e.g., half-unfolded) and a second position for storage (e.g., folded) when not used. In one embodiment, such exemplary distributed sources can be replaced by a track and a moving x-ray source.

Geometric Calibration

Figure 21:
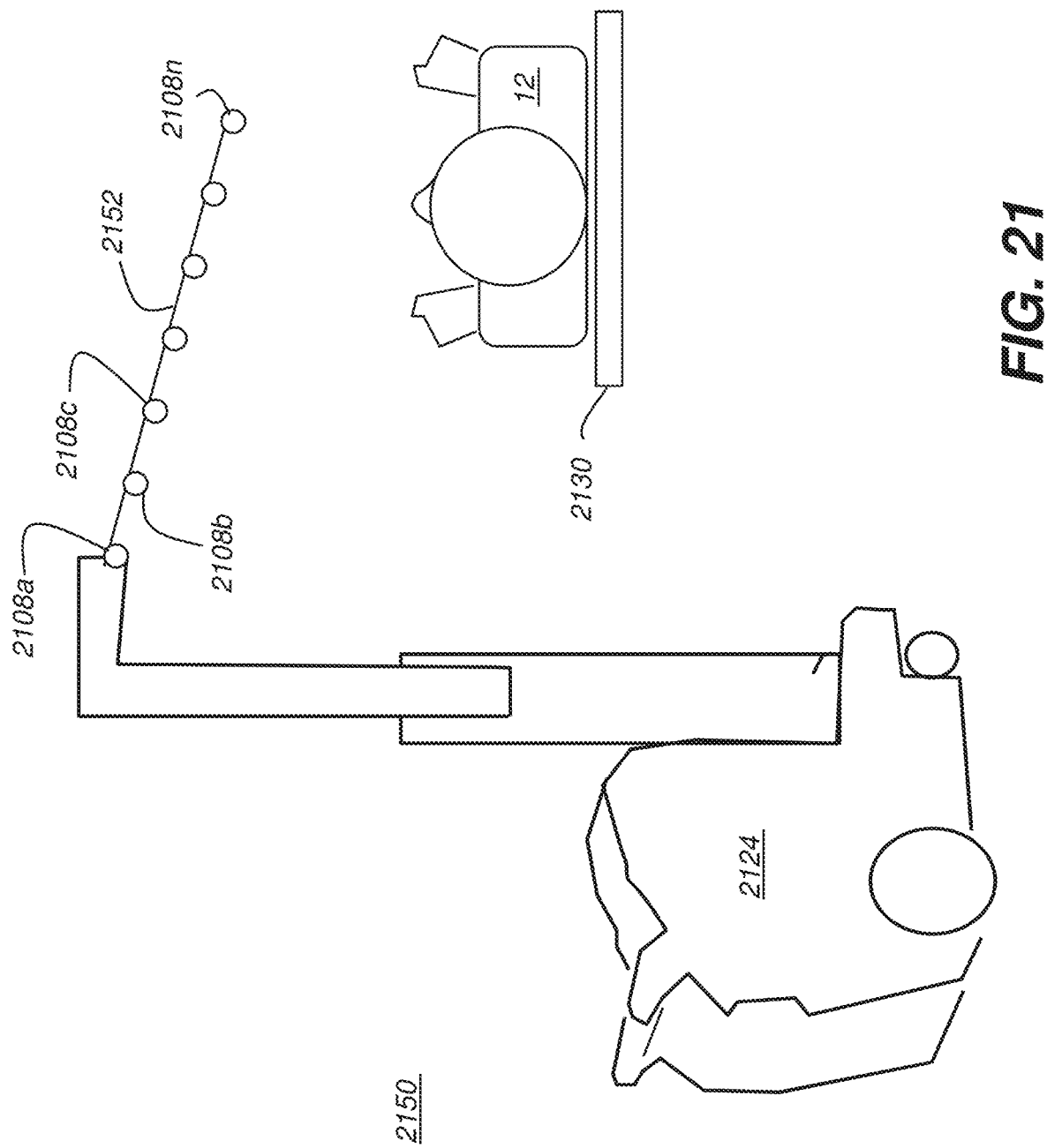
FIG. 21 is a schematic showing the spatially decoupled arrangement of detector and x-ray sources for a mobile tomosynthesis system.

For a bedside mobile tomosynthesis apparatus 2150, as shown in the schematic diagram of FIG. 21, the detector 2130 and x-ray sources 2108a, 2108b, 2108c, . . . 2108n are spatially decoupled. The position of the source(s) along a track 2152 is known, but the orientation and location of the track relative to the detector 2130 is not accurately known. Sources can be provided on a track extending from a cart 2124, for example. The orientation of the track can be recovered from a single fiducial marker whose 3D location is uncalibrated or, if the 3D location of the fiducial marker is known, then the both orientation and 3D location of the track can be recovered from the projected fiducial marker data in the tomosynthesis projections.

Alternately, a single source can be transported along linear or curved track 2152 and energized for projection image capture at discrete locations along the track, such as at the locations indicated for sources 2108a, 2108b, 2108c, . . . 2108n.

Figure 22A:
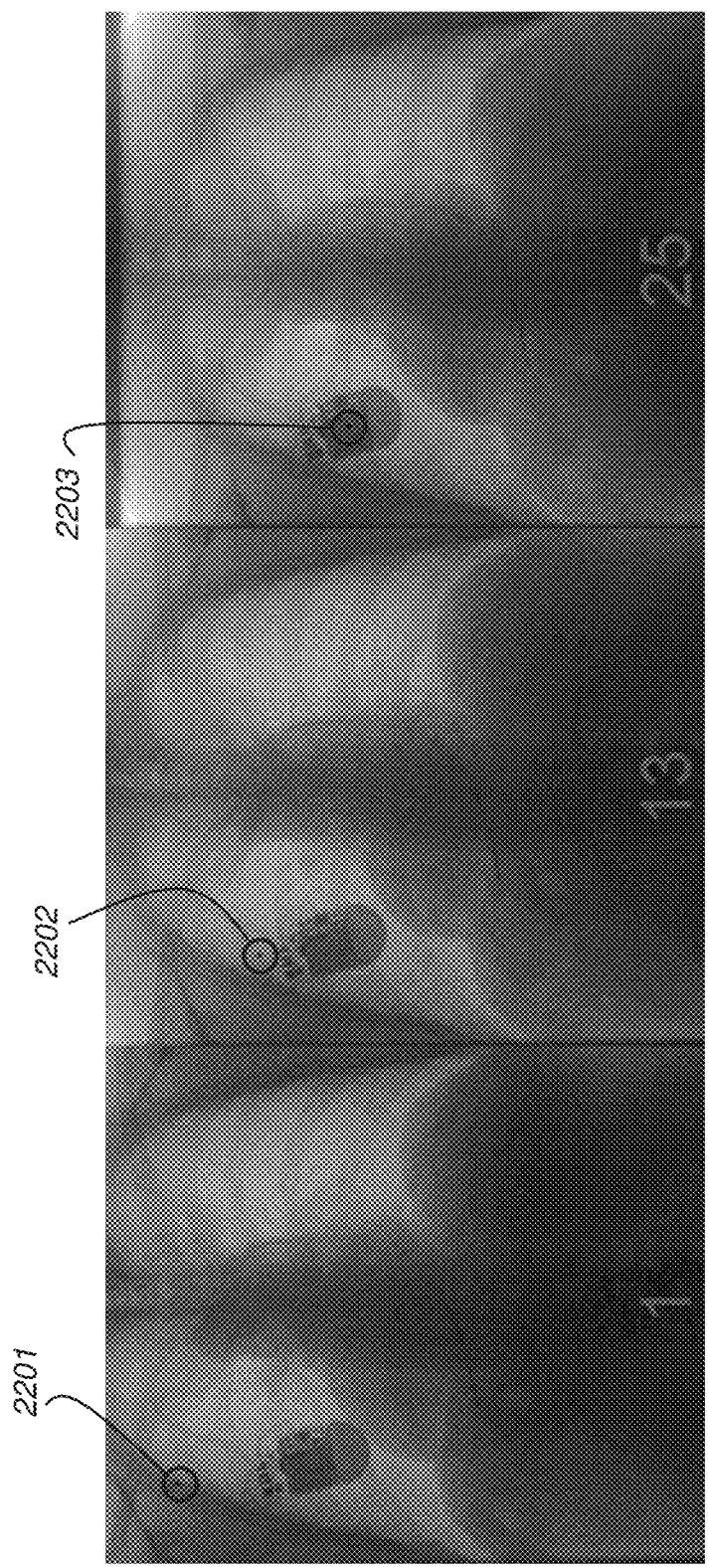
FIGS. 22A and 22B show selected images from a tomosynthesis sequence.
Figure 22B:
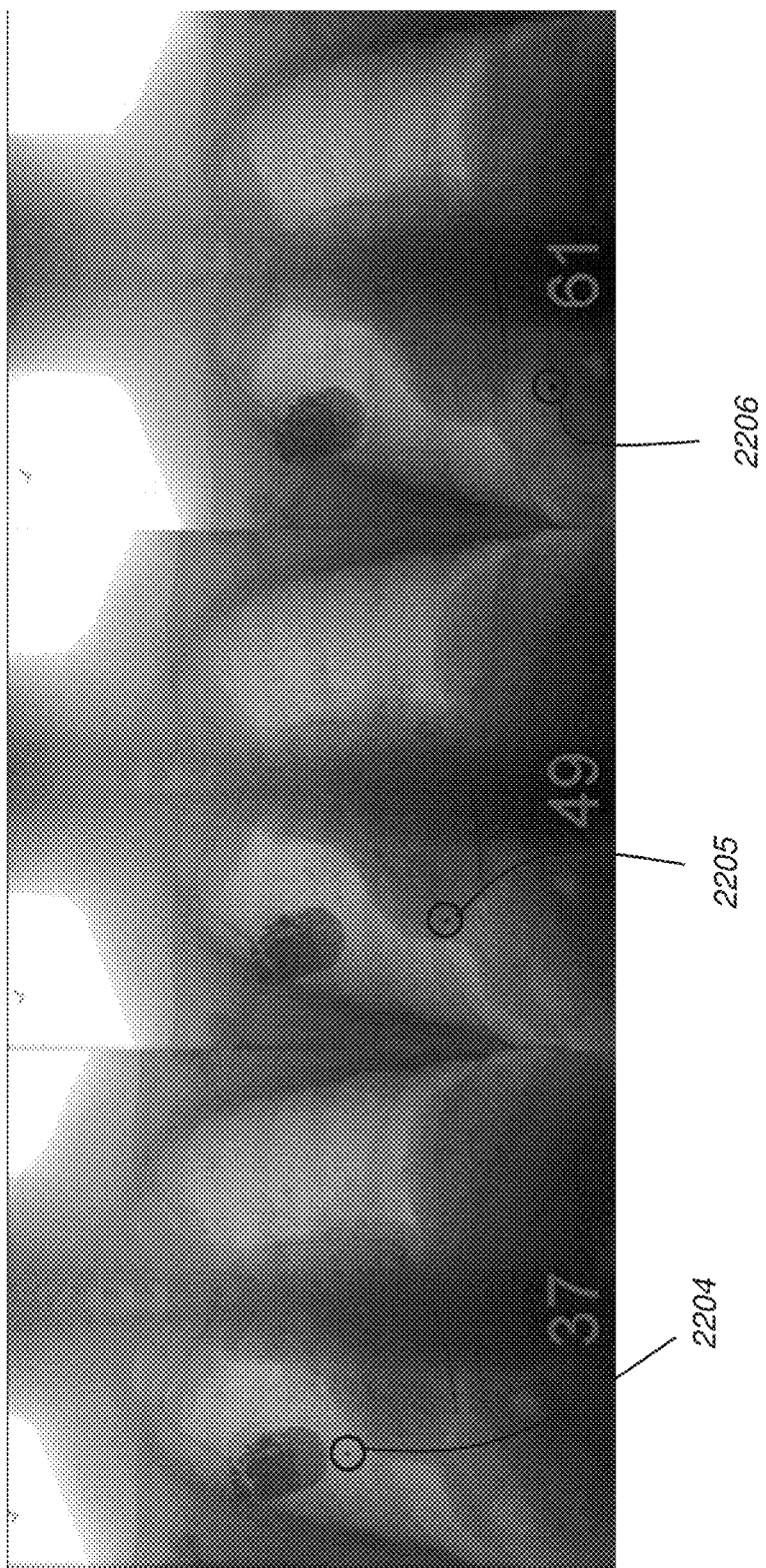

By way of example, the sequence of images shown in FIGS. 22A and 22B are selected images taken from a series of 2D projection images for a tomosynthesis system. FIG. 22A shows, from left to right, projection images #1, #13, and #25 in the tomosynthesis sequence, having Circles 2201, 2202, and 2203, respectively. FIG. 22B shows, from left to right, projection images #37, #49, and #61 in the tomosynthesis sequence, having Circles 2204, 2205, and 2206, respectively. Circles 2201, 2202, 2203, 2204, 2205, and 2206 indicate the position of an image marker or fiducial, such as a metal BB or other radio-opaque spherical object, in the progression of images in the tomosynthesis series.

Three projection images that include fiducial markers can provide sufficient information for geometric calibration, provided the location of the fiducial marker relative to the x-ray source or relative to the detector is known. Geometric calibration for tomosynthesis calculates five unknown values, related to relative angles, distance, and translation between source and detector.

Fiducial markers can be positioned at different locations in the field of view of the tomosynthesis imaging system. The selected position should be one that is imaged from at least three different positions of the source; preferably, the marker is in the field of view for each projection image in the tomosynthesis series.

Figure 23A:
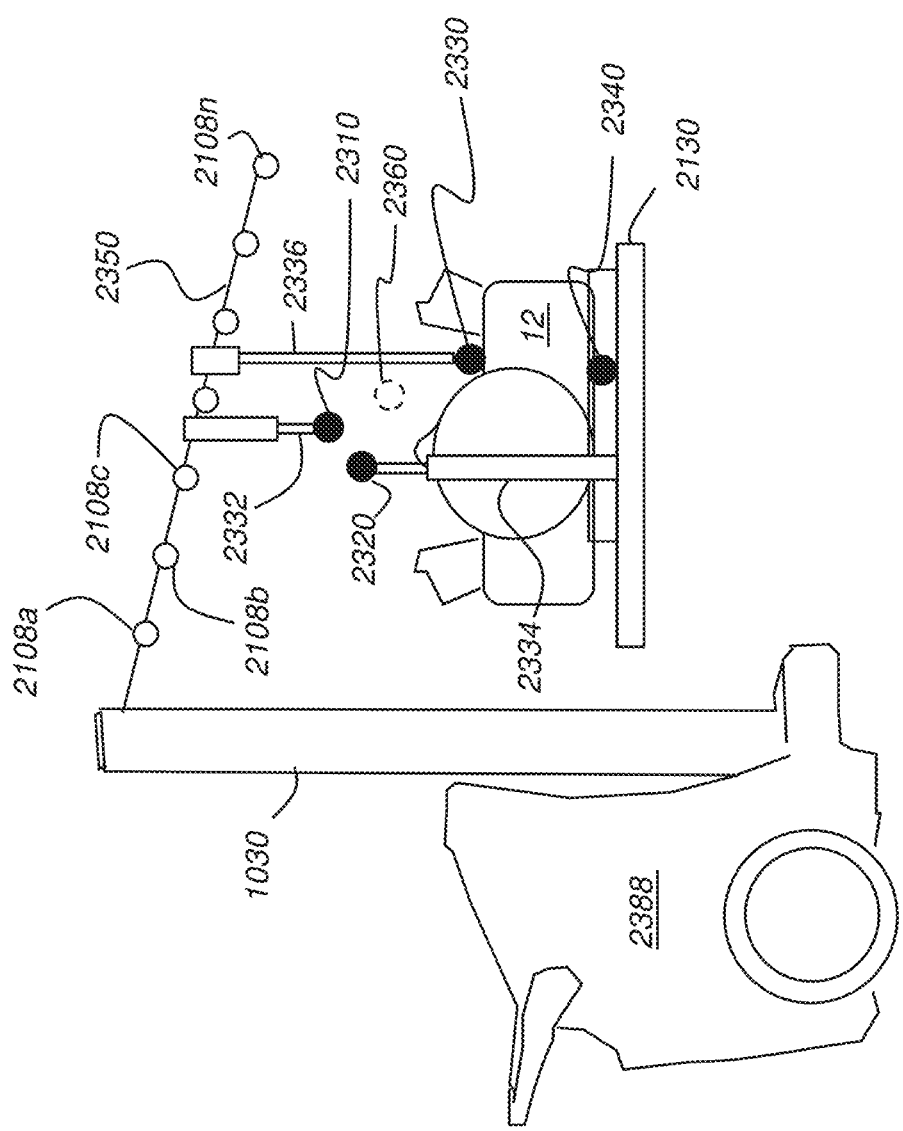
FIG. 23A is a schematic diagram that shows possible positioning of fiducial markers for acquiring geometric calibration information for bedside tomosynthesis.

The schematic diagram of FIG. 23A shows possible positioning of fiducial markers provided from a mobile radiography apparatus 2388 in order to provide geometric calibration information for bedside tomosynthesis. A fiducial marker 2310 can be extended from the x-ray source, such as positioned by attachment using a telescoping wand 2332 that extends outward by a measured distance from a track 2350.

Figure 23C:
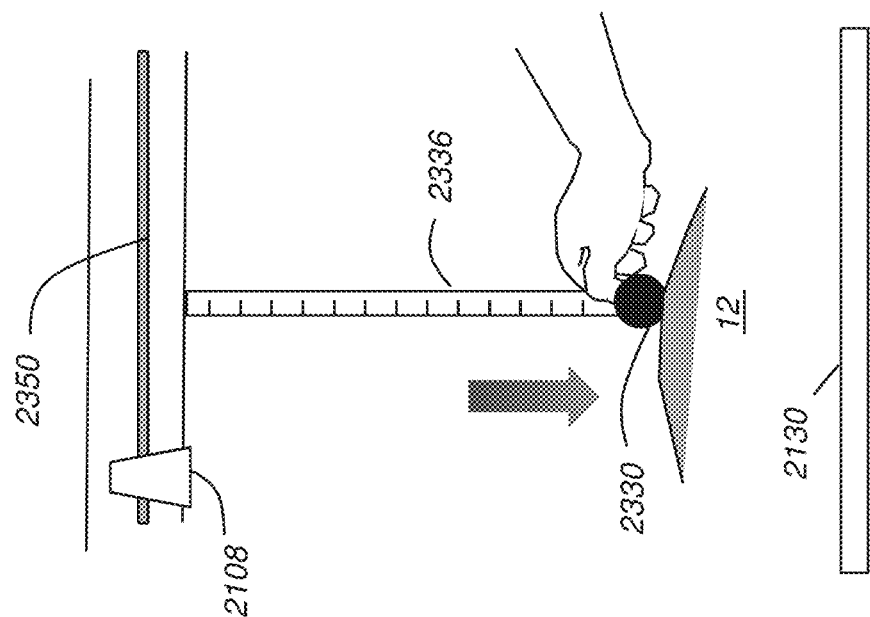
FIGS. 23B and 23C show use of a retractable tape for measuring source to marker distance according to an embodiment of the present disclosure.
Figure 23B:
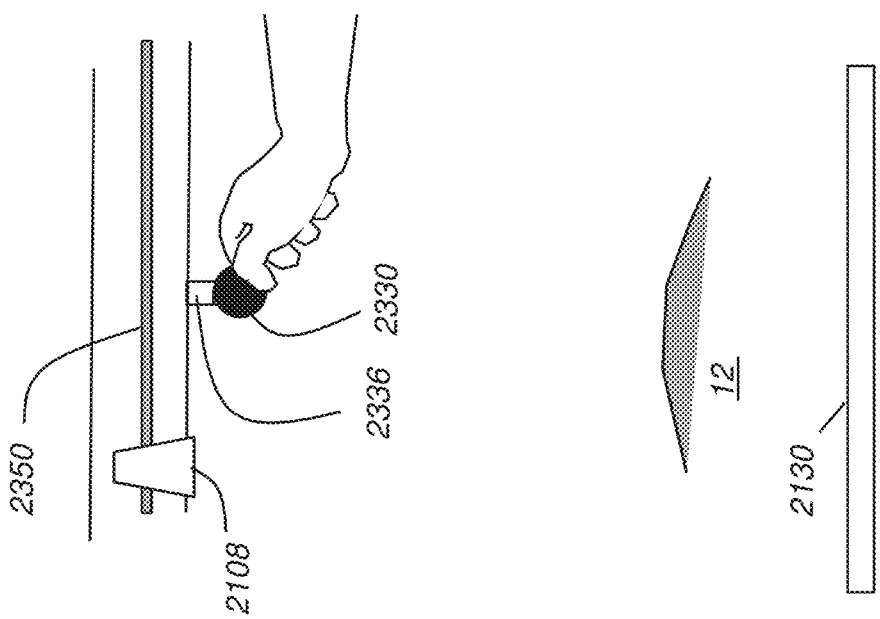

As shown in more detail in FIGS. 23B and 23C, a retractable tape 2336 can be extended outward from track 2350 for positioning fiducial marker 2330 against the patient 12 and providing a distance measurement to the marker 2330 from a source 2108. Tape 2336 can be retracted to release the marker and to leave marker 2330 in place in an embodiment. Alternately, tape 2336 can be formed from a radio-transparent material that allows the tape to remain extended during acquisition of the tomosynthesis image series.

According to an embodiment of the present disclosure, tape 2336 remains in contact with the marker and is configured to extend and retract slightly with the patient's breathing cycle, providing information on cyclic movement of the chest or of other anatomy related to breathing or other involuntary or unintentional patient movement. The function of tape 2336 for measuring source-to-marker distance can alternately be provided using a length of cord with appropriate dimensional markings. Various arrangements can allow fiducial marker 2330 to be suspended from track 2350 or from the x-ray source(s); this can include arrangements that employ gravity and that define a vertical distance between the source and the marker. The measuring apparatus can also retract after depositing the fiducial marker 2330 at a specific location following measurement.

Alternately, or in combination with markers extending from the source, a fiducial marker 2320 can extend outward from detector 2130 at a measured distance using an extendable ruler 2334, such as a stiff retractable tape or other extending device, or can extend from the mobile radiography cart. A fiducial marker 2330 can be positioned on the patient 12, with manual or automated measurement of the distance between marker 2330 and detector 2130. A fiducial marker 2340 can also between interspersed between patient 12 and the detector 2130 by embedding or encasing the fiducial marker 2340 into a block of x-ray transparent material, such as a block of Lucite™. This allows the marker 2340 to be spaced apart from the detector by a fixed distance.

Figure 23D:
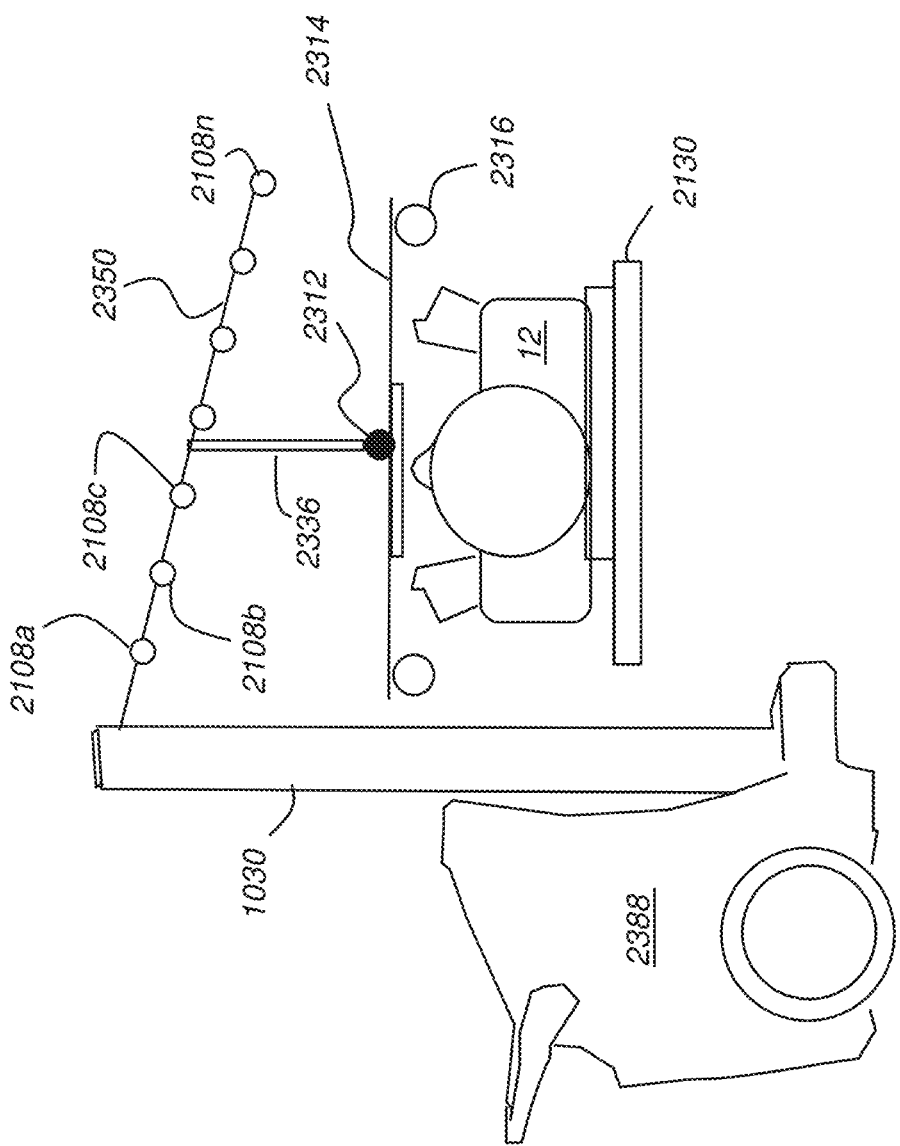
FIG. 23D is a schematic diagram showing positioning of a fiducial marker on a tray or other support structure that is independent of the mobile radiography apparatus.

As shown in dashed line representation in FIG. 23A, one or more fiducial markers 2360 can optionally be positioned at some location between the detector 2130 and x-ray sources in track 2350, wherein the relative distance and location coordinates may not be known. This arrangement can enable some positioning data to be calculated; however, information on source-to-image distance cannot be calculated using known image analysis techniques. In another alternate embodiment, as shown in FIG. 23D, a tray 2314 or other support rests on rails 2316 of a hospital bed or other structure that is separate from the mobile radiography apparatus 2388. This type of arrangement enables a marker 2312 to be maintained in a position that is independent of the x-ray system itself, not affected by movement factors such as patient respiration and not affected by equipment vibration due to actuators or other devices. Tape 2336 can be used to measure the distance between x-ray sources and marker 2312.

The projected fiducial marker location in the 2-D projection images (FIGS. 22A, 22B) can be located, either automatically or with manual assistance from the operator. The location and orientation of the x-ray source assembly can then be computed using an optimization routine along with the projected fiducial marker locations and the assumed relative geometry between the x-ray sources. The projected fiducial markers need to be found in at least three projection images in order to recover the location and orientation of the x-ray source assembly.

For a known position of a fiducial marker, such as at a number of the positions represented in FIG. 23A, for example, the spatial location can be expressed as coordinates:

(x, y, z) wherein z is height from the detector.

Figure 24:
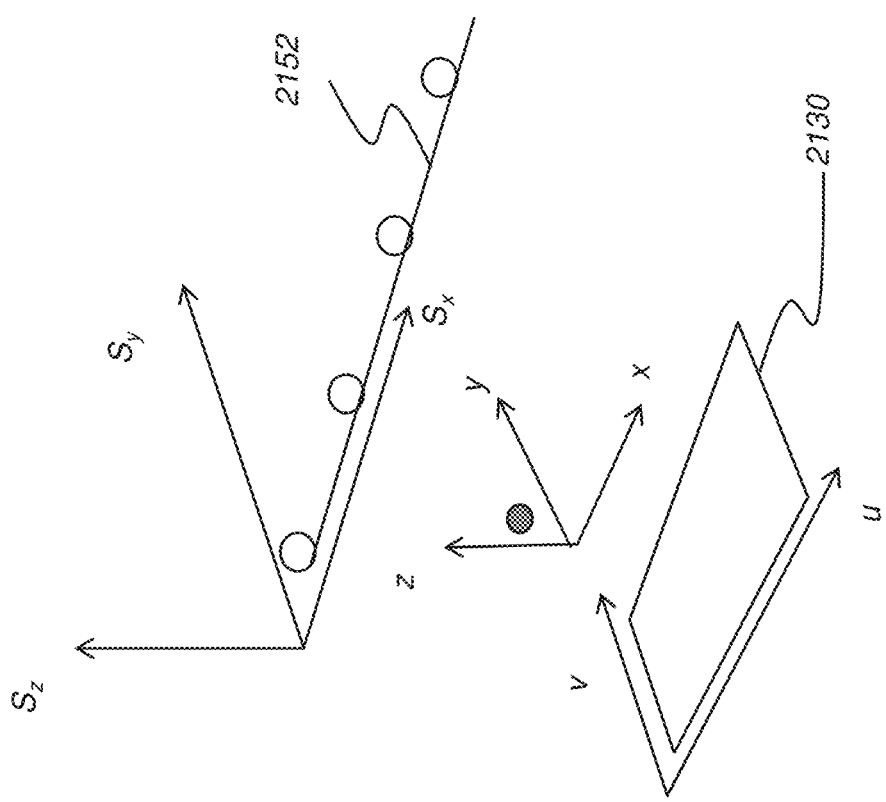
FIG. 24 is a diagram that shows the coordinate systems for source, detector, and fiducial marker.

For reference, FIG. 24 shows the coordinate systems for source, detector, and fiducial marker. Computing the source path and distance relative to the detector performs various transformations that relate these coordinate systems to each other.

For a linear array or source path and relative movement of the source positions in only one direction, as shown in the example of FIG. 23A, the coordinates for each source can be simplified to:

$$(\widehat{S_x}, 0, 0)$$

The following shows a transform of source position coordinates to the imaging system (x, y, z) coordinates:

$$\begin{bmatrix} S_x \\ S_y \\ S_z \end{bmatrix} = A \begin{bmatrix} \widehat{S_x} \\ 0 \\ 0 \end{bmatrix}$$

wherein A is a matrix that gives rotation and translation transformation relative to the source positions. Rotation is $\theta z$, $\theta y$ and translation $t_x$, $t_y$, $t_z$.

To determine coordinates (u, v) for a projection of the fiducial marker onto the detector for source coordinates ($S_x$, $S_y$, $S_z$), the following computation can be used:

$$u = \frac{xS_z - zS_x}{S_z - z}$$

$$v = \frac{yS_z - zS_y}{S_z - z}$$

In order to compute positional translation and angular rotation, an energy minimization can be used, for example:

$$E = \frac{1}{2} \sum_{m=1}^{n} (u(\vec{\theta}, \vec{t}) - u_m)^2 + (v(\vec{\theta}, \vec{t}) - v_m)^2$$

wherein vectors for rotation and translation, respectively, are:

$$\vec{\theta} = (\theta_y, \theta_z)$$

$$\vec{t} = (t_x, t_y, t_z)$$

Optionally, once the calibration data has been computed and before reconstructing the object, the projected fiducial markers can be removed from the projection image using masking or using an inpainting algorithm, techniques familiar to those skilled in the imaging arts.

Figure 25:
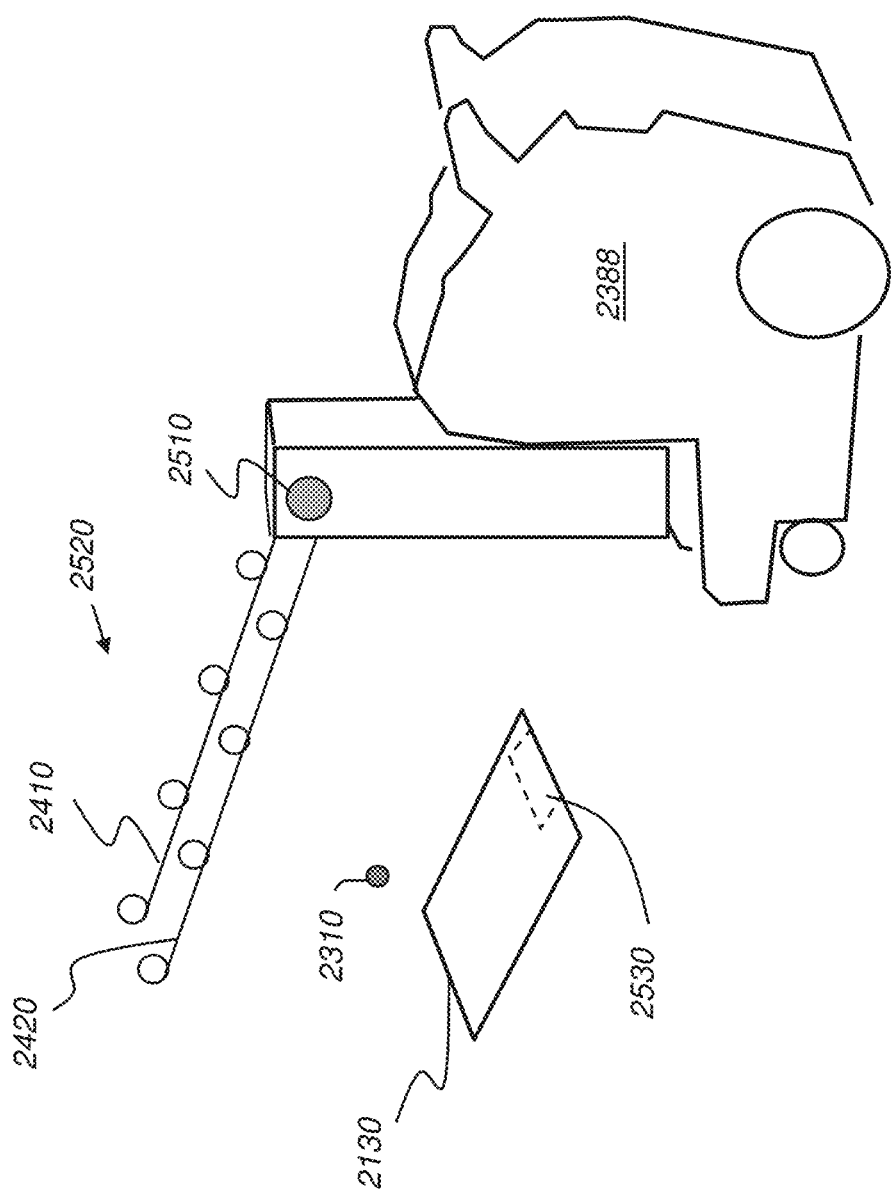
FIG. 25 is a schematic diagram that shows an alternate arrangement of x ray sources, disposed along two linear tracks.

The schematic diagram of FIG. 25 shows an alternate arrangement of x ray sources, disposed along two linear tracks 2410, 2420, providing a 2-D array of sources. Where tracks 2410 and 2420 are co-planar, calculation of source-to-image distance can be simplified using triangularization. Images acquired using sources along the first track 2410 and images acquired using sources from the second track 2420 can be used to compute the relative coordinates of sources and detector with a 2-D arrangement. Other 2-D arrangements can include a circular or angular array, for example.

FIG. 25 also shows a positioning indicator 2510 that can be provided on a mobile radiography apparatus 2388 for indicating suitable position of an x-ray source array 2520 relative to the plane that contains detector 2130. Processing logic on apparatus 2388 senses positional information from the detector 2130, such as information from level-sensing or gyroscopic sensors 2530 provided within detector 2130. Information on the angle and positioning of array 2520 that extends from the cart can also be detected. Wireless or wired signals from detector 2130 can indicate, for example, orientation of detector 2130 in order to indicate amount of offset from level. Calculations performed by processing logic on mobile radiography apparatus 2388 can then use the positional information to determine optimal positioning of array 2520 components, such as to align tracks 2410, 2420 in parallel with detector 2130. Indicator 2510 can be illuminated as an aid to angular displacement needed or achieved, either by manual adjustment of track 2410 angles or using one or more actuators.

Figure 26:
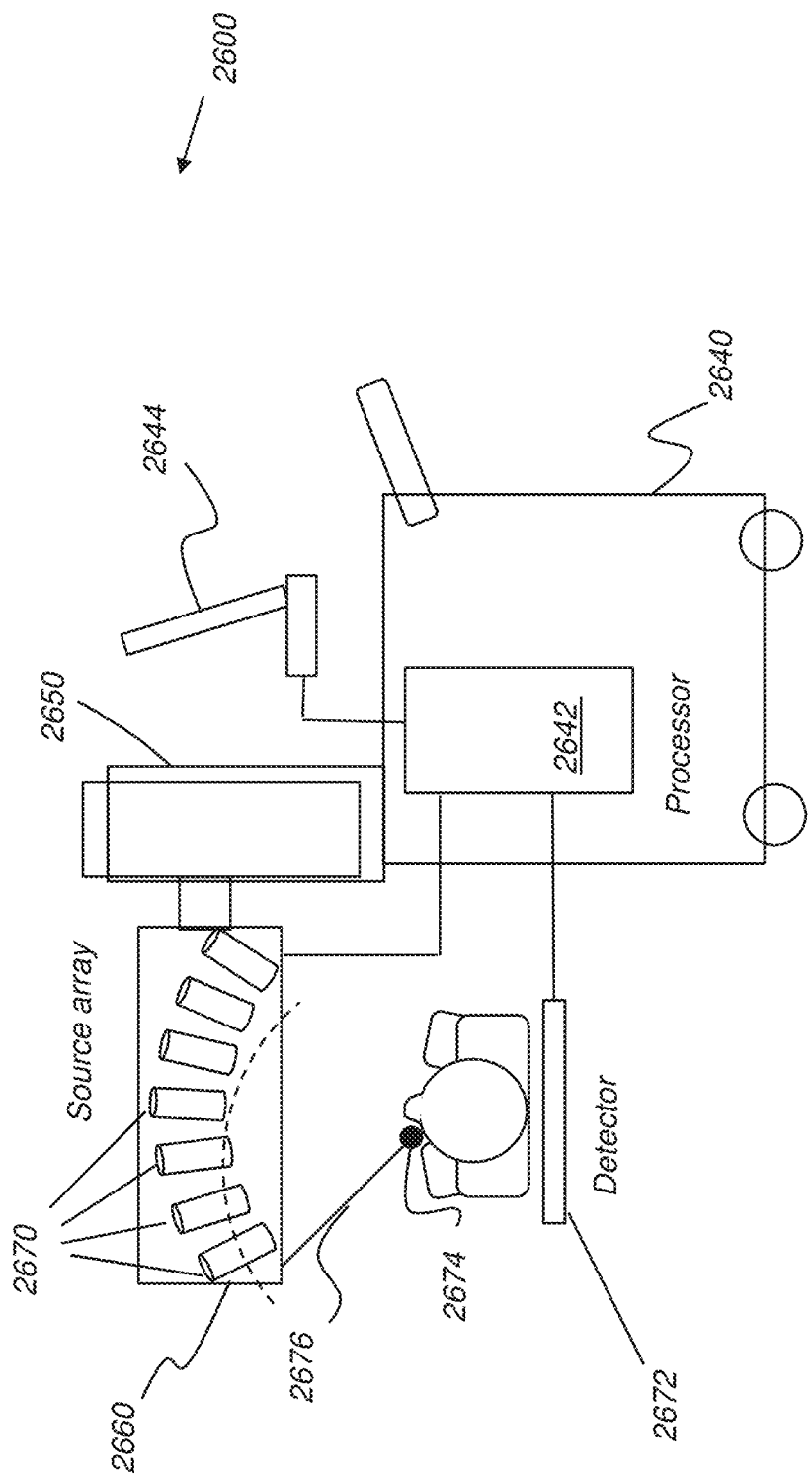
FIG. 26 is a schematic diagram that shows a mobile radiography apparatus according to an alternate embodiment of the present disclosure, having a cart that houses a processor and that has an operator display.
Figure 27:
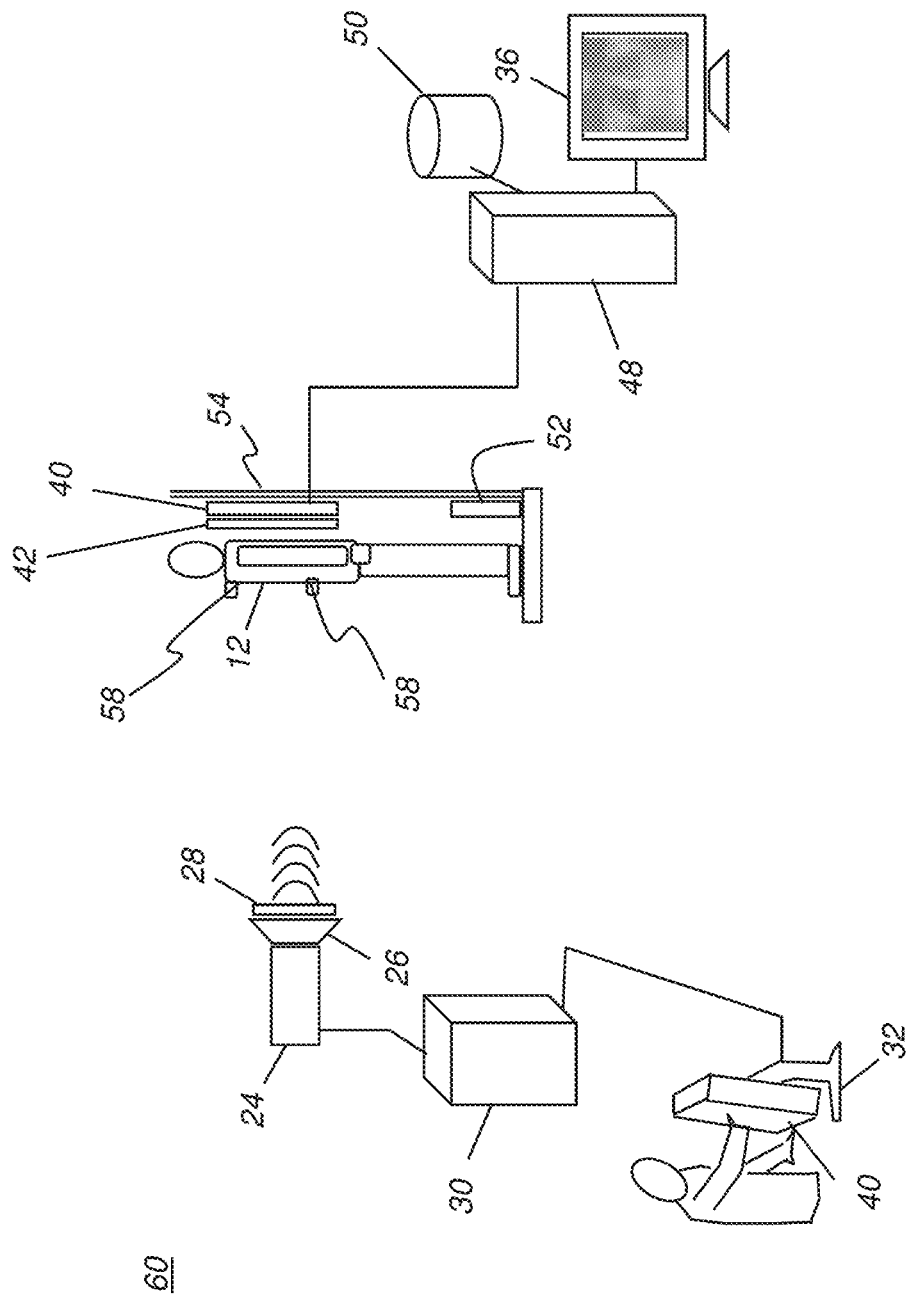
FIG. 27 is a schematic diagram showing a system using a bucky for tomosynthesis imaging.

The schematic diagram of FIG. 26 shows a mobile radiography apparatus 2600 according to an alternate embodiment, having a cart 2640 that houses a processor 2642 and has an operator display 2644. Extending from a collapsible column 2650 is a source array 2660 that includes a number of x-ray sources 2670 for individually directing radiation toward a detector 2672. A fiducial marker 2674 is extended from array 2660, such as on an extendable arm 2676, for example, providing marker 2674 at a known distance from array 2660 for positioning calculation. The position of marker 2674 can be sensed using any of a number of types of angular or linear extension sensors, well known to those skilled in the positioning arts. Extendable arm 2676 can extend from any portion of the mobile radiography apparatus 2600, such as from the cart chassis, boom, or column, for example. Referring to FIG. 27, there is shown a schematic diagram of an imaging apparatus 60 for providing chest x-ray tomosynthesis imaging of a patient 12 according to an embodiment of the present invention. An x-ray tube 24 provides the needed exposure radiation for imaging, under the control of control circuitry 30 that has an operator console 32 for entry of setup and operation commands from the technician. X-ray tube 24 has a collimator 26 that controls the angular and spatial distribution of radiation that is provided. A filter 28 is provided at the output of x-ray tube 24. Filter 28 positioning is typically controlled by control circuitry 30, such as a computer or other type of control logic processor. Imaging apparatus 60 uses a single DR (digital radiography) detector 40 that has a grid 42 for scatter compensation. A transport apparatus 52 moves the DR detector 40 to successive positions along a wall bucky 54. A DR imaging processor 48 obtains the digital data from DR detector 40 and performs the image processing steps for the obtained image data. A display 36 in communication with DR imaging processor 48, or other output device, then displays a rendering of the obtained and processed tomosynthesis image content. A computer-accessible memory 50 enables processing and storage of the obtained and processed image data. One or more fiducial markers 58 can be placed within the field of view and used to assist in geometric calibration.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for geometric calibration of a radiography apparatus, the method executed by a computer, comprising:
   disposing at least one radio-opaque marker in a field of view of the radiography apparatus;
   acquiring a series of tomosynthesis projection images of patient anatomy from a detector from different x-ray source positions along a scan path;
   identifying at least three tomosynthesis projection images from the series of tomosynthesis projection images and identifying a position of the at least one radio-opaque marker in each of the at least three tomosynthesis projection images;
   calculating a spatial and angular geometry of an x-ray source and a detector according to the positions of the at least one radio-opaque marker in each of the at least three tomosynthesis projection images;
   reconstructing a tomosynthesis image according to the calculated spatial and angular geometry; and
   displaying, storing, or transmitting a rendering of the reconstructed tomosynthesis image.

2. The method of claim 1, further comprising measuring and recording a distance from the at least one radio-opaque marker to either the x-ray source or the detector.

3. The method of claim 1, wherein acquiring the series of tomosynthesis projection images comprises translating the x-ray source along a linear source path.

4. The method of claim 1, wherein acquiring the series of tomosynthesis projection images comprises translating the x-ray source along a curved source path.

5. The method of claim 1, wherein acquiring the series of tomosynthesis projection images comprises acquiring the series of tomosynthesis projection images using an array of x-ray sources.

6. The method of claim 5, wherein disposing the at least one radio-opaque marker in the field of view of the radiography apparatus comprises extending or suspending the at least one radio-opaque marker from the array of x-ray sources.

7. The method of claim 5, further comprising positioning the array along a single line.

8. The method of claim 5, further comprising positioning the array of x-ray sources in a rectangular pattern.

9. The method of claim 5, further comprising positioning the array of x-ray sources in a curved or arcuate pattern.

10. The method of claim 1, wherein the at least one radio-opaque marker is embedded in a radio-transparent material.

11. The method of claim 1, wherein acquiring a series of tomosynthesis projection images of patient anatomy includes
acquiring a series of tomosynthesis projection images of at least a portion of a patient's chest.

12. The method of claim 1, further comprising removing the imaged at least one radio-opaque marker from the series of tomosynthesis projection images prior to reconstructing the tomosynthesis image.

13. A portable radiographic imaging apparatus, comprising:
a mobile cart;
a processor in the mobile cart;
a column attached to the mobile cart;
a detector in communication with the processor in the mobile cart, the detector defining an imaging field;
one or more x-ray sources supported by the column and positionable to direct radiation toward the detector over successive angular positions;
a fiducial marker extending into the imaging field of the detector; and
a measurement apparatus for measuring a distance between the one or more x-ray sources and the fiducial marker.

14. The portable radiographic imaging apparatus of claim 13, wherein the fiducial marker extends from the one or more x-ray sources.

15. The portable radiographic imaging apparatus of claim 13, wherein the mobile cart further comprises:
a logic processor that receives input data on detector positioning; and
an indicator in signal communication with the logic processor and energizable to guide operator positioning of the one or more x-ray sources for volume imaging.

16. The portable radiographic imaging apparatus of claim 13, wherein the measurement apparatus extends from the one or more x-ray sources.

17. The portable radiographic imaging apparatus of claim 13, further comprising a track, wherein the fiducial marker extends from the track, and wherein the track transports the one or more x-ray sources between angular positions.

18. The portable radiographic imaging apparatus of claim 13, wherein the fiducial marker extends from the detector.

* * * * *

UNITED STATES PATENT AND TRADEMARK OFFICE
CERTIFICATE OF CORRECTION

PATENT NO. : 10,743,822 B2  
APPLICATION NO. : 16/022864  
DATED : August 18, 2020  
INVENTOR(S) : Richard A. Simon et al.

Page 1 of 1

It is certified that error appears in the above-identified patent and that said Letters Patent is hereby corrected as shown below:

In the Specification

Column 14, Line 35    Please replace "$\begin{bmatrix} S_x \\ S_y \\ S_z \end{bmatrix} = A \begin{bmatrix} \widehat{S_x} \\ 0 \\ 0 \end{bmatrix}$," with --$\begin{bmatrix} S_x \\ S_y \\ S_\approx \end{bmatrix} = A \begin{bmatrix} \widehat{S_x} \\ 0 \\ 0 \end{bmatrix}$--

Signed and Sealed this  
Twenty-second Day of September, 2020

Andrei Iancu  
*Director of the United States Patent and Trademark Office*